US009579060B1

United States Patent
Lisy et al.

(10) Patent No.: US 9,579,060 B1
(45) Date of Patent: Feb. 28, 2017

(54) HEAD-MOUNTED PHYSIOLOGICAL SIGNAL MONITORING SYSTEM, DEVICES AND METHODS

(71) Applicants: Frederick J. Lisy, Euclid, OH (US); Anthony Opperman, Cleveland, OH (US); David D. Dashevsky, Cleveland, OH (US)

(72) Inventors: Frederick J. Lisy, Euclid, OH (US); Anthony Opperman, Cleveland, OH (US); David D. Dashevsky, Cleveland, OH (US)

(73) Assignee: Orbitol Research Inc., Cleveland, OH (US)

( * ) Notice: Subject to any disclaimer, the term of this patent is extended or adjusted under 35 U.S.C. 154(b) by 49 days.

(21) Appl. No.: 14/571,930

(22) Filed: Dec. 16, 2014

Related U.S. Application Data

(60) Provisional application No. 61/940,902, filed on Feb. 18, 2014.

(51) Int. Cl.
*A61B 5/00* (2006.01)
*A61B 5/0408* (2006.01)
*B05D 3/00* (2006.01)

(52) U.S. Cl.
CPC .......... *A61B 5/6803* (2013.01); *A61B 5/0022* (2013.01); *A61B 5/04085* (2013.01); *A61B 5/746* (2013.01); *B05D 3/002* (2013.01)

(58) Field of Classification Search
CPC .... A61N 1/04; A61N 1/0541; A61N 1/36032; A61N 2/02
See application file for complete search history.

(56) References Cited

U.S. PATENT DOCUMENTS

| | | | |
|---|---|---|---|
| 4,592,370 A | 6/1986 | Lee et al. | |
| 4,601,294 A | 7/1986 | Danby et al. | |
| 4,741,344 A | 5/1988 | Danby et al. | |
| 5,076,281 A | 12/1991 | Gavish | |
| 5,314,389 A | 5/1994 | Dotan | |
| 6,712,762 B1 * | 3/2004 | Lichter | A61B 5/7203 128/920 |
| 6,782,283 B2 | 8/2004 | Schmidt et al. | |
| 7,631,968 B1 | 12/2009 | Dobson et al. | |

(Continued)

FOREIGN PATENT DOCUMENTS

CN 102657523 A 9/2012
EP 1983364 A1 4/2008
(Continued)

OTHER PUBLICATIONS

David Da He, "A wearable heart monitor at the ear using Ballistocardiogram (BCG) and Electrocardiogram (ECG) with a nanowatt ECG hearbeat detection circuit", MIT Ph.D. thesis, Feb. 2013.

(Continued)

*Primary Examiner* — Omeed Alizada
(74) *Attorney, Agent, or Firm* — Brian Kulkowski

(57) ABSTRACT

Hat, helmet, and other headgear apparatus includes dry electrophysiological electrodes and, optionally, other physiological and/or environmental sensors to measure signals such as ECG from the head of a subject. Methods of use of such apparatus to provide fitness, health, or other measured or derived, estimated, or predicted metrics are also disclosed.

17 Claims, 13 Drawing Sheets

(56) References Cited

U.S. PATENT DOCUMENTS

| | | |
|---|---|---|
| 7,677,723 B2 | 3/2010 | Howell et al. |
| 7,877,126 B2 | 1/2011 | Hannula et al. |
| 8,184,068 B1 | 5/2012 | Rhodes et al. |
| 8,467,562 B2 | 6/2013 | Wada |
| 8,593,795 B1 | 11/2013 | Chi |
| 8,655,004 B2 | 2/2014 | Prest et al. |
| 2003/0195588 A1 | 10/2003 | Fischell et al. |
| 2006/0094974 A1 | 5/2006 | Cain |
| 2008/0171945 A1 | 7/2008 | Dotter |
| 2009/0097689 A1 | 4/2009 | Prest et al. |
| 2012/0203077 A1 | 8/2012 | He et al. |
| 2012/0209101 A1 | 8/2012 | Kidmose et al. |
| 2013/0274583 A1* | 10/2013 | Heck .................... A61B 5/0488 600/383 |
| 2014/0051044 A1* | 2/2014 | Badower ................. A61B 5/00 434/236 |
| 2014/0128690 A1 | 5/2014 | LeBoeuf |

FOREIGN PATENT DOCUMENTS

| EP | 2116183 A1 | 5/2008 |
|---|---|---|
| EP | 2388680 A1 | 5/2010 |

OTHER PUBLICATIONS

Orion Buske et al., "HeartBeat: Design and DEvelopment of a headphone-mounted infrared heart rate monitor", University of Washington research paper, Jun. 6, 2009.

S.F. LeBoeuf et al., "Earbud-based sensor for the assessment of energy expenditure, HR, and VO2max." abstract, Med Sci. Sports Exerc., May 2014, http://www.ncbi.nlm.nih.gov/pubmed/24743110.

Meir Magal et al., "Validity and Reliability of an Audio Headset Earbud Sensor for Heart Rate Measurements During Exercise" presentation abstract, ACSM Annual Meeting—World Congress on Exercise is Medicine, May 31, 2012, San Francisco, California, USA.

Mary Ann Bauer-Home, "Valencell PerformTek white paper", Jan. 6, 2013.

"The Dash—Wireless Smart in Ear Headphones by Bragi LLC" from kickstarter.com, 2014.

\* cited by examiner

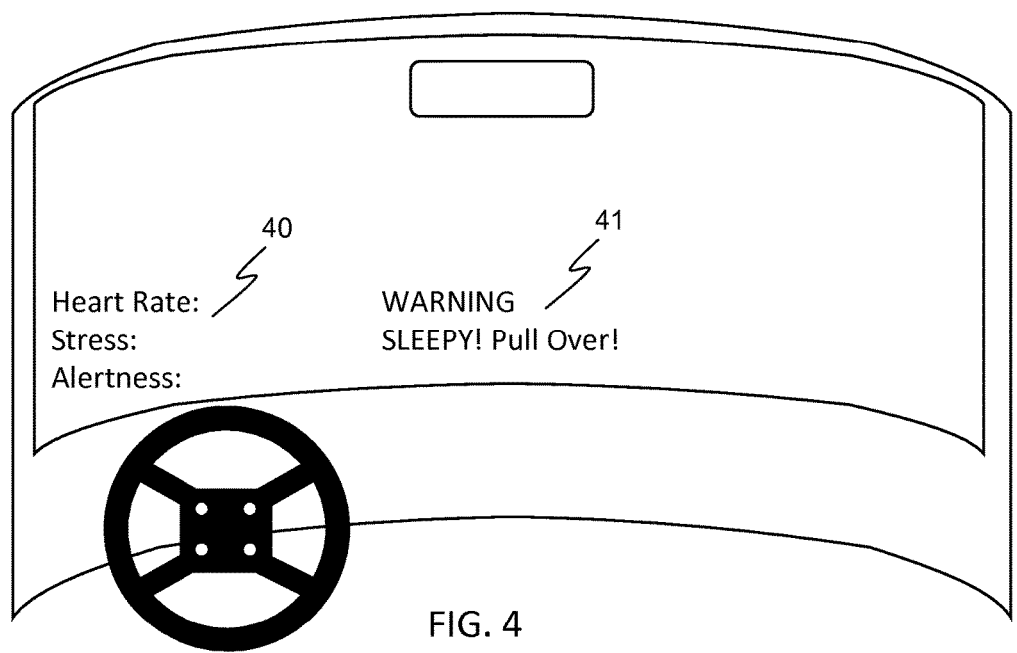
FIG. 4
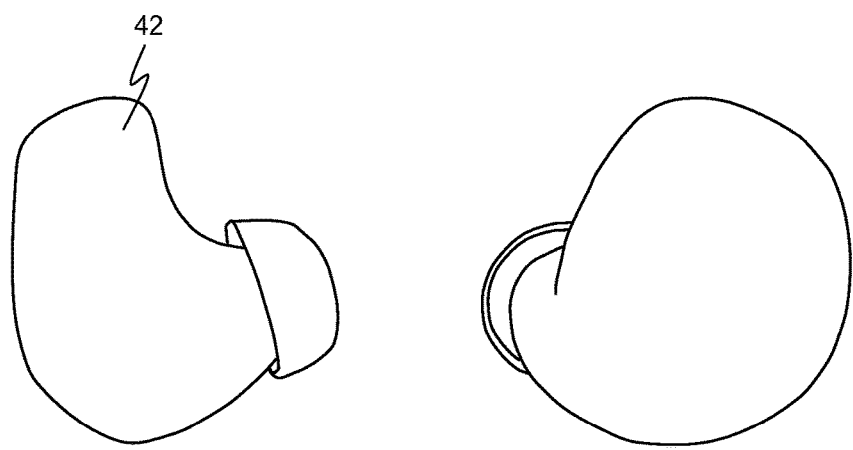

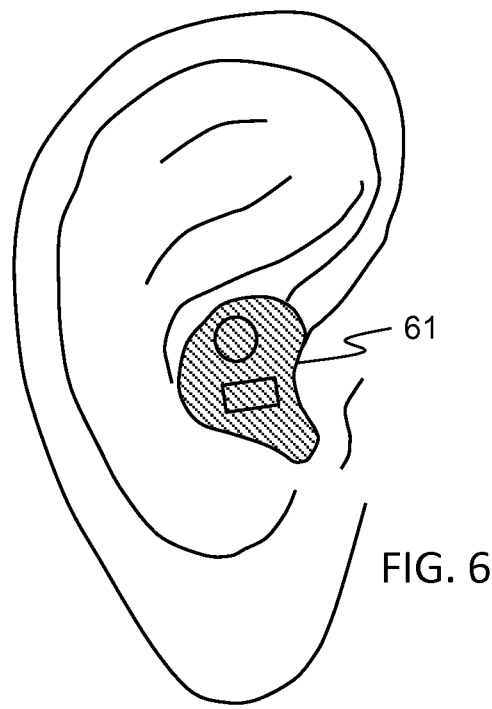
FIG. 6
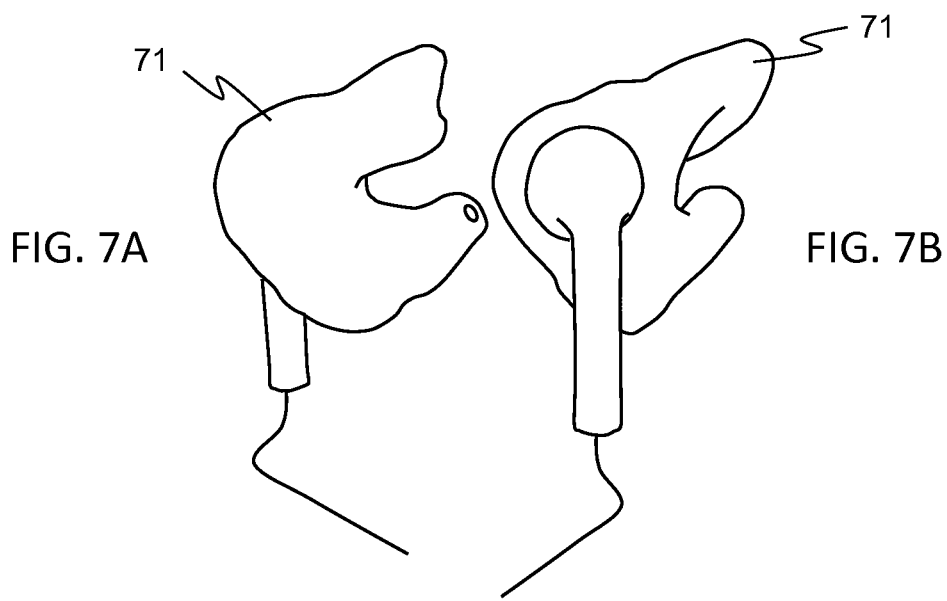
FIG. 7A
FIG. 7B

HEAD-MOUNTED PHYSIOLOGICAL SIGNAL MONITORING SYSTEM, DEVICES AND METHODS

CROSS-REFERENCE TO RELATED APPLICATIONS

This application claims priority to U.S. provisional patent application No. 61/940,902, filed Feb. 18, 2014.

BACKGROUND OF THE INVENTION

1. Field of the Invention

The present invention relates to monitoring apparatuses worn by subject and methods of using the apparatuses to physiological signals from the subject. The present invention further relates to physiologic monitoring systems that monitor physiological signals and process the signals in order to provide various forms of feedback to the user or another person. The present invention further relates to the monitoring and processing of physiological signals from a subject to provide measurements, metrics, information, data, messages, or warnings to the user based on the monitored physiological signals and related to the subject's overall health, physical performance, concentration or alertness state, and the like.

2. Technical Background

Presently, there no commercially or otherwise available systems for accurately, consistently, efficaciously and conveniently monitoring many physiological signals from a subject while the subject is performing physical activity, particularly robust physical activity including strenuous exercise. In order to obtain physiological signals under harsh or strenuous physical conditions, systems either require a large degree of preparation, attachment, and securing of sensors to the subject's body, or they suffer from disjointed, inaccurate, or noisy signals being obtained, and thus requiring large degrees of signal processing. In the growing market of physical activity for health, sport, competition, training, and the like, there are no products that are able to accurately obtain strong, clear physiological signals and provide a large series of data and information based on those signals, while still providing the convenience of a simple wearable that can be donned and doffed as easily as a piece of clothing or a fashion accessory.

It is therefore an object of the present invention to provide systems, devices and methods for acquiring signals from the human body, particularly from a subject's head, using external or surface sensors requiring little or no preparation, such as abrading the skin, surgical implantation or attachment, adhesives or electrolytic fluids or gels applied directly to the skin to aid in signal conduction, or the like. It is a further object of the present invention to allow for such easy signal acquisition of any and all biopotential physiological signals, including, but not limited to electrocardiogram (ECG), electromyogram (EMG), electrooculogram (EOG), electroencephalogram (EEG), partial pressure of oxygen and or carbon dioxide, blood oxygenation, blood pressure, body conductance, body resistance, galvanic skin response, body potential sensors, temperature (both body and ambient), and the like, as well as environmental signals relating to the conditions surrounding the subject's body including motion signals (e.g., from accelerometers, gyroscopes). It is especially an object of the present invention to provide apparatus which can cleanly acquire both EOG and ECG signals from the head of the subject and to use these signals in both a user interface navigation and also in deriving fitness metrics and reporting those metrics to the subject or others.

It is still further an object of the present invention to provide the systems, devices and methods in a portable manner. Portability refers to the preferred ability for the subject to easily carry or wear the systems or devices, or for such to be readily attached to the subject, his or her clothing or other accessories, or otherwise easily donned and worn/transported/used during strenuous physical activity. Portability also further requires the systems and devices of the present invention to preferably include a contained power system, data storage and processing components, and the ability to transmit or otherwise telemeter signals from the systems or devices to separate electronic components, potentially over great distances, such as to remotely located servers or devices.

It is still further an object of the present invention to provide the systems, devices and methods in a manner that requires reduced or eliminated power recharging requirements, through the provision of energy harvesting components and steps which can generate part or all of the needed operational power from environmental or bodily energy sources.

SUMMARY OF THE INVENTION

Because the head is far from the sources of electrophysiological activities sought to be measured, e.g., ECG, it is often overlooked as a point of collection for such signals. However, the inventors have discovered that the head actually provides a superior signal collection site because of (1) the absence of large muscle groups on the head, which are sources of EMG-type electrophysiological noise; (2) the head provides a variety of unique natural anchor points for sensors that are not uncomfortable, including in the ears, around the ears, on the bridge of the nose, and around the circumference of the head, which in turn helps to reduce motion artifact noise; and (3) the head lends itself to a number of common wearables that can be outfitted with sensors and comfortably donned and doffed with minimal effort, inconvenience, or social stigma. These insights, in combination with the inventors' innovations in dry electrophysiological sensors, have yielded the various embodiments of the present invention.

The present invention relates to head-mounted monitoring apparatuses worn by a subject and methods of using the apparatuses to acquire, process, and/or transmit physiological signals from the subject. The present invention further relates to physiologic monitoring systems that monitor physiological signals and process the signals in order to provide various forms of feedback to the subject or another person. The present invention further relates to the monitoring and processing of physiological signals from a subject to provide measurements, metrics, information, data, messages, or warnings to the subject based on the monitored physiological signals and related to the subject's overall health, physical performance, and the like.

The systems, devices, and methods of the present invention are designed for use in operations of many varieties. Preferably, the system may be used, or adapted for use, with any head-mounted wearable, including hats, helmets, eyewear, headbands, earphones, earbuds, or the like. In various embodiments the system collects one or more of (1) physiological signals, (2) ambient/environmental signals, and (3) system signals to track the physiological conditions, metrics and performance of the subject. Ambient, environmental, and system data may include, but is not limited to, pressures, temperatures, g-force, altitude, depth, geographical position, and the like. Physiological data such as the subject's ventilation, fractional concentration of expired oxygen ($FEO_2$), fractional concentration of expired carbon dioxide ($FECO_2$), breath-by-breath volume (BV), breath frequency (BF), electrocardiogram (ECG), electroencephalogram (EEG), electrooculogram (EOG), heart rate, skin temperature (including using sensors that collect temperature data from multiple skin sites for algorithmic combination of this data to produce more accurate skin temperature readings), galvanic skin response, and blood oxygen saturation ($SpO_2$) are among the many types of data, profiles and metrics that can be acquired alone or in combination by the various embodiments of the present invention.

Various embodiments of this system are differentiated from traditional systems such as, for example, other physiological monitoring systems, particularly heart rate sensors, which rely on inaccurate ECG signals corrupted by large amounts of noise, artifacts, and variation due to the conditions under which they are used, or others which utilize optical sensors to read physiological signals from the subject's inner ear. The present invention, contrary to these other systems, acquires stronger, cleaner signals from the subject's body, including ECG signals. The invention is able to do so through the use of novel platforms making advantageous use of superior body anchor points as well as novel sensor types, configurations and arrangements; processing combinations of acquired signals in novel ways to achieve higher-quality data streams for analysis; and enhanced features that promote greater comfort, wearability, and usability, which in turn promote more consistent and longer-term use and thus provide more data and more useful data from which new metrics may be derived. Various embodiments may further include various platforms for the sensors, such sensors including temperature sensors, heat flux sensors, respiration sensors, pressure sensors, physiological electrodes such as ECG, EMG, EOG, and EEG, a pulse oximeter, body conductance sensors, body resistance sensors, accelerometers, gyroscopes, body potential sensors, blood pressure sensors, impedance sensors, microphones, body and blood chemistry sensors, galvanic skin sensor and the like, which can be incorporated for example into or on caps, glasses or eyewear, sweatbands, headphones, in-ear headphones or ear buds, hats, helmets, and the like. The sensors of the present invention are able to effectively record signals through or among areas of the subject body that other sensors cannot, such as on hairy portions of the subject, like the scalp, or sweaty portions, without preparation of the skin (abrading, removal of the hair, etc.). The sensors of the present invention are fit and able to acquire heart rate signals and heart rate variability. The sensors can be tethered by physical electrical connection or linked wirelessly. The wireless link can be through radio frequency, optical link, acoustics and the like. The sensor signals are transmitted through an appropriate link to an electronic data acquisition or controller or other subsystem that might in certain embodiments contain either a small on-board processor and/or other electronic components for not only receiving the sensor(s) signal, but also for possibly filtering, digitizing, converting, calculating and the like of the signal and data into information related to the subject's physiological condition and in certain embodiments using that information or data to control the delivery of gases, medication, and/or other physical stimulation to the subject. Preferably, the data acquisition or controller systems, as well as power and transmission systems are contained in or on the device or system itself, such as embedded into a pair of eyeglasses or sunglasses, rather than requiring a separate processing unit. The device or system may additionally pair with other sensor systems attached to the subject or worn by the subject, for example an arm or torso sensor or an electronic device such as a digital watch or smart watch, or cellular phone or smart phone, and where the invention fuses data from the sensors on the various devices to provide a more complete and robust set of data as well as recommendations and/or warnings.

The monitoring apparatus is preferably a small, wearable system containing at least one sensor for detecting and measuring particular conditions of the subject. The apparatus may include one or more of the wearables listed in this application, including but not limited to earphones (including earbuds and headphones), headgear (including hats, helmets, caps, headbands, and masks), eyewear (including eyeglasses, sunglasses, and eyeglasses frames), watches, phones, wristbands, chest bands, arm bands, ankle bands, shoes, clipped-on devices, and hand-held devices. Preferably, if sensors are implemented across multiple devices, each device is either wired to one or more other devices or the devices are independently equipped with processors and electronic components for two-way wireless transmission of data and instructions, by radio or otherwise, to the various other components as required for data collection and analysis. Preferably, the sensors make use of the natural pressure provided by the wearables to hold the sensors securely in place at natural anchor points on the body. Most preferably, those points are inside the ear and on the temples.

In one embodiment, the invention is an in-ear apparatus for acquiring physiological signals comprising at least one earbud, the earbud having at least one soundspeaker and at least one dry electrophysiological electrode, the dry electrode comprising a plurality of low aspect ratio protruding surface features. Preferably, the surface features have an aspect ratio of less than 1.5. Preferably, the surface features are shaped and arranged as an array of bumps. Also preferably, the earbud further comprises at least one other sensor for pressure, temperature, g-force, altitude, galvanic skin response, blood oxygenation, movement, ambient sound, or the speech sound of the user. Preferably, this in-ear embodiment uses an IR tympanic temperature sensor to aid in producing energy expenditure models and/or kinematic models. Further preferably, the earbud further comprises a rechargeable battery. Further preferably, the earbud further comprises an electronic radio component capable of wireless two-way communication with at least one other device. Further preferably, the dry electrode is formed by a first step of forming an electrode shape including surface features by injection molding, casting or depositing a material into a mold, followed by a second step of coating at least a portion of the electrode shape with a conductive or semi-conductive film. Alternatively, the dry electrode is formed by coating, deposition, or impregnation of a conductive material onto or into a pliant material that has been molded or etched to have the surface features. In such case, preferably, the conductive material is silver/silver chloride and the pliant material is a polymer, elastomer, foam, or rubber. Further preferably, the at least one earbud is adapted to be mechanically anchored entirely within the ear, without external support. Alternately, the at least one earbud is adapted to be anchored with support of a hook adapted to be fitted around the ear, and preferably at least one other physiological or environmental sensor is positioned on the hook. Further preferably, the at least one earbud further comprises an ambient microphone adapted to measure ambient sound signals, a computer processor adapted to process the ambient sound signals so as to generate corresponding noise cancelling sound signals provided through the at least one soundspeaker, and a user interface adapted to permit the subject to be provided with a non-ambient sound substantially free of ambient sound, a transparent ambient sound free of non-ambient sound, or any continuous mix between the two, through the at least one soundspeaker.

In another embodiment, the invention is a method of collecting ECG signals of a subject comprising inserting into the subject's ear an in-ear apparatus for acquiring physiological signals comprising at least one earbud, the earbud having at least one soundspeaker and at least one dry electrode, the dry electrode comprising a plurality of low aspect ratio protruding surface features; measuring with the dry electrode an electrophysiological signal; amplifying and filtering the electrophysiological signal to produce an ECG signal; and transmitting or storing the ECG signal for collection. Preferably, the ECG signals are further processed to determine heart rate. Further preferably, the ECG signals are further processed to determine one or more of heart rate variability, respiration rate as derived from the ECG modulation and/or respiratory sinus arrhythmia or a combination of the two. Further preferably, at least one other metric is derived based at least in part on the ECG signals and at least in part on one other measured physiological or environmental parameter. Also preferably, the heart rate metric, heart rate variability metric, and/or the at least one other derived metric are reported to the subject and/or form the basis of a notice or warning delivered to the subject by a automatic output selected from the group consisting of a visual display, an audible alarm, speech, a mild electrical shock, or an ambient or localized temperature change, or a change in the lighting permitted to enter the eyes of the subject.

In yet another embodiment, the invention is a method of providing health information to a subject comprising inserting into the subject's ear an in-ear apparatus for acquiring physiological signals comprising at least one earbud, the earbud having at least one soundspeaker, at least one dry electrode, and at least one other physiological sensor of a different type than electrophysiological, the dry electrode comprising a plurality of low aspect ratio protruding surface features; measuring with the dry electrode an electrophysiological signal; substantially simultaneously, measuring with the at least one other physiological sensor a second signal indicative of a physiological parameter; and deriving a physiological metric using at least in part both the electrophysiological signal and the second signal, wherein the metric is indicative of metabolism, heat loss, calories expended, stress, alertness, concentration, or sleep stage. Optionally, the method further comprises the step of delivering an alert or warning to the subject based at least in part on the derived physiological metric through one or more of a visual display, an audible signal, or a change in ambient or localized temperature or light. Also optionally, the method further comprises the step of delivering an alert or warning to a person remote from the subject via wireless communication; this step may be done either before or after detecting that the alert or warning was not heeded by the subject.

In still another embodiment, the invention is a headgear apparatus for acquiring electrophysiological signals comprising a hat or helmet comprising elastic or contoured foam portions adapted to fit snugly to, and place light pressure on, the head of a subject, and a plurality of dry electrophysiological electrodes along the elastic or contoured foam portions, the dry electrodes each comprising a plurality of low aspect ratio protruding surface features. Preferably, the surface features have an aspect ratio of less than 1.5. Preferably, the surface features are shaped and arranged as an array of bumps. Also preferably, the headgear apparatus further comprises at least one other sensor for pressure, temperature, g-force, altitude, galvanic skin response, blood oxygenation, movement, ambient sound, or the speech sound of the user. Further preferably, the headgear apparatus further comprises a rechargeable battery. Further preferably, the headgear apparatus further comprises an electronic radio component capable of wireless two-way communication with at least one other device. Further preferably, the dry electrodes are formed by a first step of forming an electrode shape including surface features by injection molding, casting or depositing a material into a mold, followed by a second step of coating at least a portion of the electrode shape with a conductive or semi-conductive film. Alternatively, the dry electrodes are formed by coating, deposition, or impregnation of a conductive material onto or into a pliant material that has been molded or etched to have the surface features. In such case, preferably, the conductive material is silver/silver chloride and the pliant material is a polymer, elastomer, foam, or rubber.

In still yet another embodiment, the invention is a method of collecting ECG signals of a subject comprising placing on the subject's head a headgear apparatus for acquiring electrophysiological signals, the headgear apparatus consisting of a hat or helmet comprising elastic or contoured foam portions adapted to fit snugly to, and place light pressure on, the head of a subject, and a plurality of dry electrodes along the elastic or contoured foam portions, the dry electrodes each comprising a plurality of low aspect ratio protruding surface features; measuring with the dry electrodes electrophysiological signals; amplifying and filtering the electrophysiological signals to produce ECG signals; and transmitting or storing the ECG signals for collection. Preferably, the ECG signals are further processed to determine heart rate. Further preferably the ECG signals are further processed to determine heart rate variability. Further preferably, at least one other metric is derived based at least in part on the ECG signals and at least in part on one other measured physiological or environmental parameter. Also preferably, the heart rate metric, heart rate variability metric, and/or the at least one other derived metric are reported to the subject and/or form the basis of a notice or warning delivered to the subject by a output selected from the group consisting of a visual display, an audible alarm, speech, a mild electrical shock, or an ambient or localized temperature change, or a change in the lighting permitted to enter the eyes of the subject.

In even still another embodiment, the invention is a method of providing health information to a subject comprising placing on the subject's head a headgear apparatus for acquiring electrophysiological signals a hat or helmet comprising elastic or contoured foam portions adapted to fit snugly to, and place light pressure on, the head of a subject, a plurality of dry electrodes along the elastic or contoured foam portions, and at least one other physiological sensor of a different type than electrophysiological, the dry electrodes each comprising a plurality of low aspect ratio protruding surface features; measuring with the dry electrodes electrophysiological signals; substantially simultaneously, measuring with the at least one other physiological sensor a non-electrophysiological signal indicative of a physiological parameter; deriving at least one physiological metric using at least in part both the electrophysiological signal and the non-electrophysiological signal, wherein the metric is indicative of metabolism, heat loss, calories expended, stress, alertness, concentration, or sleep stage. Preferably, the method includes the further step of determining, with a computer processor, when the at least one derived metric has exceeded a threshold or has exhibited a predefined or learned pattern; and automatically providing a stimulus to the subject via a display, alarm, vibrator, buzzer, or stimulus electrode either integrated into the eyeglasses apparatus or integrated into a separate device adapted to be kept on the person of the subject and in communication with the eyeglasses apparatus through either a wired or wireless link.

In even yet another embodiment, the invention is a hat for acquiring electrophysiological signals comprising contoured foam portions adapted to fit snugly to the head of a subject, and to place light pressure on the head at various points; a plurality of dry electrodes along the elastic portion at the points of light pressure, the dry electrodes each comprising a plurality of low aspect ratio protruding surface features; and one or more electronic components for recording or transmitting signals measured by the dry electrodes wherein the pressure provided by the foam portions is sufficient to maintain good electrical contact between each of the electrodes and the skin of the subject.

In still a further embodiment, the invention is a headband or sweatband for acquiring electrophysiological signals comprising an elastic portion, adapted and shaped to fit snugly to the head of a subject, and to place light pressure on the head at various points; a plurality of dry electrodes along the elastic portion at the points of light pressure, the dry electrodes each comprising a plurality of low aspect ratio protruding surface features; and one or more electronic components for recording or transmitting signals measured by the dry electrodes wherein the pressure provided by the elastic portion is sufficient to maintain good electrical contact between each of the electrodes and the skin of the subject.

In yet a further embodiment, the invention is a skull cap, swim cap, or tight-fitting dew-rag for acquiring electrophysiological signals comprising an elastic portion, adapted and shaped to fit snugly to the head of a subject, and to place light pressure on the head at various points; a plurality of dry electrodes along the elastic portion at the points of light pressure, the dry electrodes each comprising a plurality of low aspect ratio protruding surface features; and one or more electronic components for recording or transmitting signals measured by the dry electrodes wherein the pressure provided by the elastic portion is sufficient to maintain good electrical contact between each of the electrodes and the skin of the subject.

In even a further embodiment, the invention is a helmet for acquiring electrophysiological signals comprising an elastic portion, adapted and shaped to fit snugly to the head of a subject, and to place light pressure on the head at various points; a plurality of dry electrodes along the elastic portion at the points of light pressure, the dry electrodes each comprising a plurality of low aspect ratio protruding surface features; and one or more electronic components for recording or transmitting signals measured by the dry electrodes wherein the pressure provided by the elastic portion is sufficient to maintain good electrical contact between each of the electrodes and the skin of the subject.

In now an additional embodiment, the invention is an eyewear apparatus for acquiring electrophysiological signals comprising eyeglasses frames having temple stems and having a plurality of dry electrodes along the stems, the dry electrodes each comprising a plurality of low aspect ratio protruding surface features. The eyewear apparatus may be eyeglasses, sunglasses, eyeglass frames without lenses, or a visual display device anchored by stems to the ears and/or nose. Preferably, the electrode surface features have an aspect ratio of less than 1.5. Preferably, the surface features are shaped and arranged as an array of bumps. Further preferably, each stem has at least one dry electrode adapted for placement nearer to the eyes for detecting an EOG signal and at least one dry electrode adapted for placement above the ears for detecting an ECG signal. Also preferably, the eyewear apparatus further comprises at least one other sensor for pressure, temperature, g-force, altitude, galvanic skin response, blood oxygenation, movement, ambient sound, or the speech sound of the user. Further preferably, the eyewear apparatus further comprises a rechargeable battery. Further preferably, the eyewear apparatus further comprises an electronic radio component capable of wireless two-way communication with at least one other device. Further preferably, the dry electrodes are formed by a first step of forming an electrode shape including surface features by injection molding, casting or depositing a material into a mold, followed by a second step of coating at least a portion of the electrode shape with a conductive or semi-conductive film. Alternatively, the dry electrodes are formed by coating, deposition, or impregnation of a conductive material onto or into a pliant material that has been molded or etched to have the surface features. In such case, preferably, the conductive material is silver/silver chloride and the pliant material is a polymer, elastomer, foam, or rubber. Further preferably, the eyewear apparatus further comprises a user interface that is navigable and/or operable with the detected EOG signal(s), as well as blink artifacts detected in the EOG signal(s). Further preferably, the eyewear includes a visual display. Further preferably, the lenses of the eyewear are electronically darkenable, especially upon detection of a physiological, environmental, or combined physiological-environmental condition.

Optionally, the eyewear apparatus further comprises one or two earbuds connected to the stems of the glasses by wires and adapted to be mechanically anchored entirely within the ear, without external support, the earbud(s) having soundspeaker(s) and at least one of earbuds having an additional electrophysiological sensor. Further preferably, the eyewear apparatus further comprises an ambient microphone adapted to measure ambient sound signals, a computer processor adapted to process the ambient sound signals so as to generate corresponding noise cancelling sound signals provided through the soundspeaker(s), and a user interface adapted to permit the subject to be provided with a non-ambient sound substantially free of ambient sound, a transparent ambient sound free of non-ambient sound, or any continuous mix between the two, through the at least one soundspeaker.

In still an additional embodiment, the present invention is a method of collecting ECG signals of a subject comprising placing on the subject's head an eyewear apparatus for acquiring physiological signals comprising eyeglasses frames having temple stems and having a plurality of dry electrodes along the stems, the dry electrodes each comprising a plurality of low aspect ratio protruding surface features; measuring with the dry electrodes electrophysiological signals; amplifying and filtering the electrophysiological signals to produce ECG signals; and transmitting or storing the ECG signals for collection. Preferably, the method also includes the step of collecting EOG signals from the subject with dry electrodes placed along the stems nearer to the eyes of the subject. Further preferably, the method includes the step of navigating and operating a user interface using the collected EOG signals. In related embodiments, preferably, EOG signals and blink rate determinations are used as a measure of the subject's level of engagement, general attention, or attentional fixation on a given object-of-attention.

In yet another embodiment, the present invention is a method of providing health information to a subject comprising placing on the subject's head an eyewear apparatus for acquiring physiological signals comprising eyeglasses frames having temple stems, having a plurality of dry electrodes along the stems, and having at least one other physiological sensor of a different type than electrophysiological, the dry electrodes each comprising a plurality of low aspect ratio protruding surface features; measuring with the dry electrodes electrophysiological signals; substantially simultaneously, measuring with the at least one other physiological sensor a non-electrophysiological signal indicative of a physiological parameter; deriving at least one physiological metric using at least in part both the electrophysiological signal and the non-electrophysiological signal, wherein the metric is indicative of metabolism, heat loss, calories expended, stress, alertness, concentration, or sleep stage. Preferably this method, further comprises the steps of determining, with a computer processor, when the at least one derived metric has exceeded a threshold or has exhibited a predefined or learned pattern; and automatically providing a stimulus to the subject via a display, alarm, vibrator, buzzer, or stimulus electrode either integrated into the eyewear apparatus or integrated into a separate device adapted to be kept on the person of the subject and in communication with the eyeglasses apparatus through either a wired or wireless link.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention. They are not, however, intended to be limiting or to illustrate all envisioned embodiments.

BRIEF DESCRIPTION OF THE DRAWINGS

FIG. 4. A wireless earbud embodiment used as a driving alert or arousal system.

FIG. 6. A hearing aid embodiment of the present invention.

FIGS. 7A-7B. A custom-molded earbud embodiment of the present invention.

Figure 1:
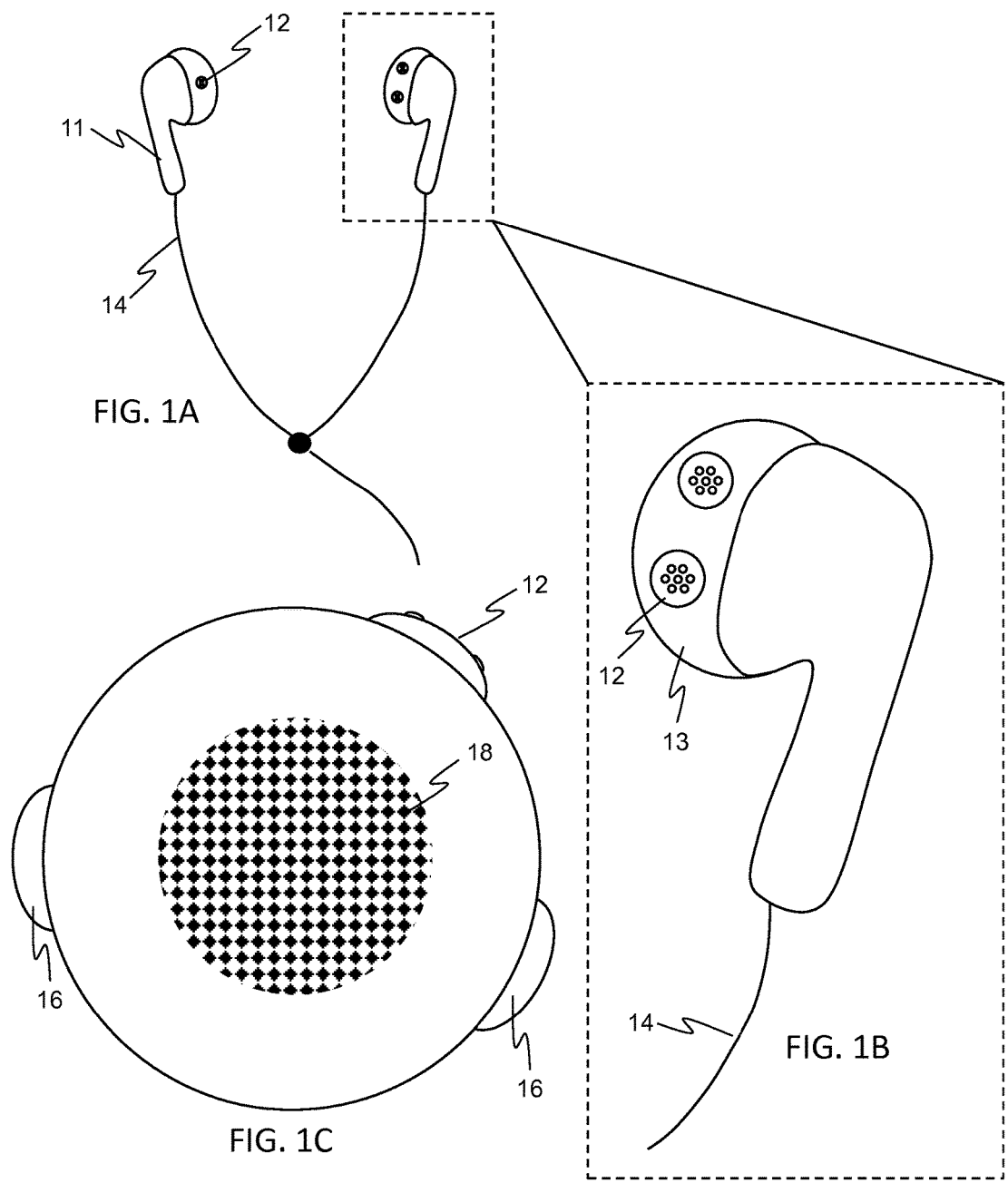
FIGS. 1A-1C. An earbud embodiment of the present invention.

DESCRIPTION OF WEARABLES, SENSORS, ACTUATORS, AND COMPUTED METRICS USED IN THE PREFERRED EMBODIMENTS

The present invention provides physiological data acquisition, processing, transmission, and/or information provision/warning apparatuses worn by a subject and methods of using the apparatuses to acquire, process, and/or transmit physiological signals from the subject. Some embodiments of the present invention further provide physiologic monitoring systems that monitor physiological signals and process the signals in order to provide various forms of feedback to the subject or another person. Some embodiments of the present invention further provide monitoring and processing of physiological signals from a subject to provide measurements, metrics, information, data, messages, or warnings to the user based on the monitored physiological signals and related to the subject's overall health, physical performance, and the like.

Various embodiments of the present invention include sensors and components for storage and/or transmission of signals integrated into a wearable that preferably anchors the sensors to the body with little or more preferably no preparation of the skin surface and preferably with no sensor attachment or setup procedure beyond the typical donning of the wearable itself. Wearables used in embodiments of the present invention include caps, glasses or eyewear, sweatbands, headphones, in-ear headphones or ear buds, hats, helmets, and the like. These wearables provide for both enforcement of proper placement and appropriate pressure on the body surface of the various sensors, including dry electrodes, used to monitor physiological parameters of the subject and/or collect environmental information, such as ambient audio data or ambient temperature data. The wearable(s) of the various embodiments may also be used to protect one or more electrical components and allow for the connection of various sensors to the electrical components within or on the wearable(s), the electrical components being for amplification, processing, storage, and/or transmission of measured sensor signals, and/or for providing feedback or stimulus to the subject, which may include audio, video, tactile, electrical, or other sensory stimulus. The wearable will preferably have electrical connections or connectors incorporated or embedded into the structure of the wearable, so that various sensors are connected to the electrical components. The wearable can be constructed from any suitable material and using any method known in the art; including, but not limited to, various types of textiles and fabrics, various types of wood, various types of plastics, various types of polymers, various types of resin, various types of ceramics, various types of metals, and various types of composite materials.

Wearables

In many embodiments the present invention consists of one or more of the following wearables having one or more of the following sensors coupled to a processor and one or more of the following actuators.

Headgear.

Headgear is defined generally as anything worn about the head, but excluding articles which are applied only to the face. Certain eyewear that wraps around the head, such as traditional glasses and goggles, but excluding pince-nez and monocles, are to be considered headgear. Headgear further includes hats, helmets, and masks that fit about the head.

Eyewear.

Eyewear includes any worn apparatus fitted to the head or face through which the eyes peer. Eyeglasses, sunglasses, goggles, monocles, pince-nez, and certain masks may be considered eyewear. Implements held up to the face for a short period in order to peer through them, such as traditional binoculars, telescopes, spyglasses, and the like are not considered eyewear for the purposes of this application.

Headphones.

Headphones consist of a pair of earphones that completely cover or largely cover the ears, and without fitting inside of the ears, joined by a band placed over the head.

Earbuds.

Earbuds consist of smaller earphones that fit inside the ears. For the purposes of this application, the term "earbud" excludes devices which enclose the ear or which substantially cover the outer surface of the ear; ear buds include only those devices which fit snugly into the outer ear canal and are there anchored. Thus, the terms "headphones" and "earbuds" should be considered to be mutually exclusive. Headphones and earbuds have both structural and functional differences that are important to this application, as headphones are not anchored to the ears in the same ways that earbuds are and can be more easily jostled and disturbed during vigorous activity such as jogging.

Hats.

Hats are headgear that fit entirely about the head and cover the head. Hats include ballcaps and knit caps.

Helmets.

Helmets are headgear that fit entirely about the head and are sufficiently rigid to protect the head from impacts. Helmets frequently have inner padding that helps to fit them to the contours of the head and further helps to absorb impacts.

Masks.

Masks are headgear that generally cover all or part of the face and function either to disguise or to protect or both. Masks have some provision to see through them in at least some conditions. A welder's mask is an example of a mask that provides protection and the ability to see through in very bright (but not dark) conditions.

Visors.

Visors are headgear that fit substantially (but not always entirely) about the head and include a front brim that acts as an eyeshade, but a visor does not totally cover the head on the top. In the context of helmets, however, the word "visor" as used in this application does not refer to a piece of headgear, but rather to a glass or glass-like piece fitting in the helmet permitting visibility through the front of the helmet while providing protection.

Gloves.

Gloves may be used to provide haptic feedback to the subject as well as to sense hand motions, postures, gestures, and/or pressures as forms of input to the device of the present invention. Preferably, the sensors and/or actuators of the gloves of the present invention are wirelessly coupled to the processor and/or sensors and/or actuators of some other device, including one or more of the other wearables described herein. Gloves are especially advantageous as input mechanisms and output actuators where the hands of the subject are occupied with a control task, as with controlling a vehicle (airplane, helicopter, automobile, bicycle, motorcycle, etc.) or other equipment. For example, a bicycle rider wearing bicycle gloves may control the other systems or devices of the present invention by squeezing certain fingers or parts of the palm, and without letting go of the bicycle handlebars.

Wristwatches.

Watches, and particularly smart watches, may be fitted with the sensors of the present invention may serve as the primary device of the present invention or more preferably may supplement or support an eyewear, earphone, headwear or other device by providing additional physiological or environmental sensors and/or by providing a user interface. In such cases the wristwatch advantageously communicates with the other device(s) of the present invention using a wireless protocol such as Bluetooth.

Sensors

The physiological and environmental sensors of the present invention include, in various embodiments, the types described in detail below.

Dry Electrodes.

Many embodiments of the present invention may utilize dry physiological electrodes to acquire many physiological signals from the subject, and in some instances to provide actuated feedback to the subject based on measurements and calculations provided by the system. The term "dry electrode" as used in this application does not refer merely to any dry apparatus or device used as an electrode, such as a dry metal plate or other dry metallic surface; rather, the dry electrodes of the present invention are designed to provide the performance associated with typical gelled, or "wet," electrophysiological electrodes. Examples of dry electrodes may be found in U.S. Pat. Nos. 6,785,569, 7,032,301, 7,032,302, 7,286,864, 7,489,959, and 7,881,764, which are incorporated by reference. Dry electrodes provide the advantage that there is no gel to dry out, no skin to abrade or clean, and that the electrode can be applied in hairy areas such as the scalp. Specifically, such advantages of many of the dry electrode embodiments incorporated from the above patents are enabled by the surface features described in said patents, which provide increased support and stability when the electrode is placed on the subject, increased ability be placed in traditionally unusual parts of the body, such as on the head or scalp where hair prevents typical electrodes from obtaining physiological signals, and which substantially eliminate the need to prepare the subject's skin or use electrolytic fluids or gels to efficaciously acquire signals. The use of dry physiological electrodes also provides uncommon reusability and the possibility for long-term/long-duration wear and/or monitoring. Thus, an earbud, hat, helmet, or eyewear having such dry electrodes can be reused virtually limitlessly and may be worn comfortably for hours or days at a time without the necessity for electrode replacement and without appreciable loss in the quality of collected signals. Additionally, if electrodes are used as the sensor(s), preferably at least two electrodes are used—one signal electrode and one reference electrode—and if further physiological signal channels are desired, the number of electrodes required will depend on whether separate reference electrodes or a single reference electrode is used, as would be understood by a person skilled in the art.

If electrodes are used to pick up electrophysiological signals, these electrodes, for example when measuring cardiac signals using electrocardiography (ECG), may be placed at specific points on the subject's body. ECG is used to measure the rate and regularity of heartbeats as well as the size and position of the chambers, any damage to the heart, and in diagnosing sleeping disorders. As the heart undergoes depolarization and repolarization, electrical currents spread throughout the body because the body acts as a volume conductor. The electrical currents generated by the heart are commonly measured by an array of preferably not more than 10 electrodes, placed on the body surface. In traditional arrangements, electrodes may be placed on each arm and leg, and six electrodes may be placed at defined locations on the chest. The specific location of each electrode on a subject's body in such traditional arrangements is well known to those skilled in the art and varies amongst individual and different types of subjects. Although a full ECG test usually involves ten electrodes, only two are required for many other applications such as sleep studies, heart rate monitoring during exercise, and many others. These may be placed on the subject's left-hand ribcage, under the armpit and on the right-hand shoulder, near the clavicle bone, or in other convenient locations on either side of the subject's body. However, for purposes of the present invention, preferably, sensors, including electrodes as sensors, are placed on various points on the subject's head in order to acquire ECG and other physiological signals. As few as two electrodes may be used, at least one for acquiring the biopotential signal and at least one as a ground electrode, but any number could be used limited only by placement locations on the subject's head, or by the desired number of channels required or desired to be acquired. In some embodiments of the present invention, preferably, ECG is acquired using dry ECG electrodes placed in or near the subject's ears; the electrodes may be mounted on or integrated into such platform wearables as earbuds, headphones, sweatbands, hats, caps, helmets, eyewear, and the like.

The dry physiological electrode sensors of the present invention can be used in a variety of applications including for measuring various biopotentials including but not limited to ECG, electroencephalogram (EEG), electromyogram (EMG), and electrooculogram (EOG), and for taking other physiological measurements, such as galvanic skin response and temperature, that can be determined from the skin or subcutaneous layers of the subject. The sensors can further be used for any other application wherein ionic potentials are measured. The ionic potentials can be acquired and transmitted via the dry electrodes in similar manners as biopotentials using a "wet" electrode, and thus various measurements and calculations can be obtained and/or performed from those potentials. Further still, the dry electrode may be used for point-to-point measurements between electrodes. Examples of these other types of applications may include, but are not limited to, blood composition measurements such as glucose or alcohol concentration, or electrical impedance measurements such as electrode impedance, skin impedance, or impedance of fluids in the body.

The dry electrodes of the present invention are applied to a subject, which can be an animal or human body having skin comprising an epidermis comprising a stratum corneum layer and lower layers of the epidermis, and a dermis. The dry electrodes of the present invention further preferably comprise at least one surface feature on the lower surface of the device, the surface that comes into contact with the subject's skin. The surface feature(s) increases the surface contact with the skin and transforms a portion of the ionic current into an electric voltage that can be transmitted through these individual surface feature(s). The surface features further enhance the stability of the device when placed on the subject's skin, and serve to decrease electrical impedance, thus facilitating transmission of a stronger, higher quality signal. Preferably, the surface feature(s) minimize(s) or eliminate(s) movement of the dry electrode with respect to the subject's skin so as to minimize or eliminate certain types of signal distortion associated with such motion (i.e., motion artifact).

The dry electrode of the present invention has an upper and a lower surface. The lower surface of the dry electrode is preferably the surface that comes into contact with the subject's skin, when the dry electrode is placed onto the subject. The lower surface may take on many shapes or arrangements, and may further include a number of surface features for displacing, cracking, or perturbing the stratum corneum or outer layer of the epidermis, for accessing the lower layers of the epidermis, thus decreasing the electrical resistance of the electrical pathway from the lower layers to the dry electrode, and/or for the achieving the other benefits mentioned above and below in this specification. These surface features may take one of many forms including, but not limited to, bumps, spikes, cones, ridges, columns, penetrators, anchors, epidermal stops and combinations thereof. The described surface features, in general, protrude from the various shaped substrates described above. Preferably, the surface features are low-profile cones, rounded bumps, or rounded bumps that are just slightly pointed at the tips (i.e., with inverted dimples). Preferably, there is at least one structure or surface feature protruding from the dry electrode's lower surface; more preferably, there are a multiplicity of such surface features arranged in an array, either evenly-spaced or in a spacing that otherwise meets the needs of the particular application (e.g., denser central spacing with gradually more diffuse spacing toward the periphery, or vice-versa). One of the important secondary functions of the configuration of surface features is to displace or move the hair, dead skin cells and/or detritus so that the surface features can better collect the electrical biopotentials generated by the body. The sizes of the surface features are also important: when surface features are too small, they cannot sufficiently compress the supper layer of skin, while when surface features are too large, they tend to be uncomfortable.

The dry electrode of the present invention further comprises an upper surface. In some embodiments of the present invention, the upper surface can have various types of connectors formed or attached on the top or upper surface of the dry electrode. The connector can simply be a common button type connection in order to connect to standard terminals for various devices or can be shaped to provide for unique connecting features in order to require special terminals to be created for the monitoring device. These connectors may be integrated into or with the upper surface or may be a separate component attached to the upper surface. Preferably, however, rather than having a connector, which may unnecessarily and uncomfortably protrude, the upper surface of the dry electrode is directly electrically connected to other components for amplifying, filtering, processing, recording, and/or transmitting acquired signals without the use of a connector element; more preferably, the dry electrodes of the present invention and their electrical connections are integrated into the structure of the wearable (earbud, hat, helmet) as much as possible so as to provide maximum comfort, simplicity, and reusability; such integrate implies manufacturing that eliminate connectors and prefers permanent connections between dry electrode elements and electrical component elements.

Various embodiments of the present invention comprise a separate encouragement ring for the dry electrode(s). The encouragement ring has an opening into which a dry electrode, or recording portion of the dry electrode, can be placed, and which allows the encouragement ring to surround and hold, preferably firmly, the recording portion. This encouragement ring provides stability to the dry electrode such that when the device is placed on a subject's skin, the ring encourages the device to become seated in contact with the subject's skin and to minimize movement of the device. This encouragement ring effectively helps to further anchor the dry electrode to the subject's skin by providing a biasing force that tends to drive or hold the device down onto the subject's skin and thus seating the device, and more importantly the surface feature(s), securely in contact with the subject's skin. This helps to increase signal quality and efficacy while minimizing artifacts, particularly movement artifacts, in the physiological signal being acquired. Additionally, the encouragement ring provides increased surface area to the upper surface of the dry electrode which allows the device to be combined with an adhesive collar or some wearable device, system or garment to be applied to the subject's skin in a more stable and secure fashion. The encouragement ring may be of any shape (such as circular or rectangular) to accommodate the wearable garment or adhesive that may be used to apply the device to a subject.

Other embodiments of the present invention may not include a separate encouragement ring, but rather have a lip which may curve up from the lower surface of the dry electrode acting like an encouragement ring, and which surrounds and provides an edge for a stamped or molded sheet metal or plastic piece. This lip provides the same function and utility as the separate encouragement ring described above, but is integrated into the dry electrode when manufactured, and thus is not separate.

Additionally or alternatively to the above-described encouragement ring, the wearables of the present invention preferably employ compressible and springy padding or cushioning which assists in gently pressing the electrode(s) or other sensor(s) against the skin of the subject so as to maximize skin-sensor contact and minimize motion artifact-causing skin-sensor movement. The electrodes may also (or alternatively) be pressed against the skin by the natural action or fit of the wearable or some component thereof. For example, the temple stems and hinges of eyewear may provide gentle pressure against a subject's head for electrodes or other sensors mounted on or integrated into the stems, or the elastic band of a ball cap or natural compression of a knit cap may provide similar inward pressure for the advantageous mounting of sensors inside those wearables.

Many embodiments of the dry electrode of the present invention, particularly those where the dry electrode is constructed of a non-conductive material, comprise a conductive coating and/or ionic compound which helps to create an electrical pathway for signals to be transferred from the subject to the monitoring equipment, and to minimize electrical impedance of the device. Conversely, some embodiments may not require or utilize a conductive coating or ionic compound at all, most notably those embodiments wherein the electrode is constructed of a conductive metal. Alternatively, some embodiments may be coated in a less expensive metallized conductive coating (typically a polymer or plastic device), and receive a conductive coating and/or ionic compound on only a portion of the device, such as just the surface feature(s). Typically, this coating is a silver/silver chloride (Ag/AgCl) coating, but it may be of any conductive or ionic compound known to those in the art presently, or later developed for such use. Alternatively, Ag/AgCl inks or other conductive inks, such as those sold by DuPont (DuPont 5874), Ercon, and the like may be used, as well as any with the appropriate electrical and/or ionic properties, and which can be compounded and used for such applications as described herein.

The Ag/AgCl coating utilized may help to ensure the dry electrodes are substantially nonpolarizable. Nonpolarizable electrodes are those in which current passes freely across the interface between the electrode and the skin, and thus require no energy to make the transition. A dry electrode utilizing Ag/AgCl is typically governed by two separate reactions: 1) oxidation of silver atoms on the electrode surface to silver ions in the material at the interface, and 2) the combination of silver ions ($Ag^+$) with chlorine ions ($Cl^-$) at the material at the interface. In this case, the material at the interface containing the chlorine ions may include biological fluids of the subject. Thus this reaction may further be enabled by the concentration of chlorine ions in biological fluids. Thus, when the dry electrode is placed in contact with the subject's skin, the Ag/AgCl coating on the device may first oxidize creating silver ions, and then those silver ions combine with free chlorine ions contained in the material at the interface including the biological fluids of the subject. This interface creates a substantially nonpolarized connection that allows for the free flow of biopotential signals from the subject into the dry electrode with a minimized impedance. Preferably, the amount of Ag/AgCl used to create these reactions and minimize electrical impedance of the device is minimized in thickness, weight, and/or surface area in order to keep manufacturing costs low.

Preferably, the conductive coating and/or ionic compound covers no more of the dry electrode than necessary, and is minimized to reduce cost of manufacturing the device. In monolithic embodiments, the conductive coating and/or ionic compound typically and traditionally can cover the entire lower surface of the dry electrode and at least some portion of the upper surface connecting the lower surface to the connector of the upper surface of the device, creating a continuous pathway of the conductive coating and/or ionic compound from the lower surface to the connector (or point of connection, in embodiments without connectors). Some embodiments provide the conductive coating and/or ionic compound on a portion of the lower surface of the device, for example only coating the center most portion of the lower surface, or coating just the tips or ends of the surface feature(s) which are in contact with the subject's skin when the device is applied to the subject. In such embodiments, preferably less than 90% of the lower surface has the conductive coating and/or ionic compound. More preferably less than 80% of the lower surface has the conductive coating and/or ionic compound. Still more preferably less than 70% of the lower surface has the conductive coating and/or ionic compound. Even more preferably less than 60% of the lower surface has the conductive coating and/or ionic compound. Even still more preferably less than 50% of the lower surface has the conductive coating and/or ionic compound. More preferably still, less than 40% of the lower surface has the conductive coating and/or ionic compound. Even still more preferably less than 30% of the lower surface has the conductive coating and/or ionic compound. Still yet more preferably, less than 20% of the lower surface has the conductive coating and/or ionic compound. Even still more preferably, less than 10% of the lower surface has the conductive coating and/or ionic compound.

In other monolithic embodiments, the coating is not applied to the lower surface of the dry electrode based the inner radius of the lower surface covered, but rather such coating is further minimized by application only to the surface features located on the lower surface. These embodiments differ from the above described embodiments because the coating here is only applied to the surface features and enough of the interstitial space between the surface features to create a web-like conductive network connecting each of the surface features to each other. In other words, the coating is not applied to the entire selected inner radius of the dry electrode, thus coating the entire inside of that radius, but is rather selectively and specifically applied to the surface features and a network connecting those surface features together. This allows the amount of coating required to be minimized even further, and thus reduce costs even further. In such embodiments, preferably less than 30% of the lower surface has the conductive coating and/or ionic compound. More preferably less than 25% of the lower surface has the conductive coating and/or ionic compound. Even more preferably less than 20% of the lower surface has the conductive coating and/or ionic compound. Still more preferably less than 15% of the lower surface has the conductive coating and/or ionic compound. Even still more preferably less than 10% of the lower surface has the conductive coating and/or ionic compound. In such embodiments, the percentage of the lower surface that is covered in the conductive coating and/or ionic compound is easily managed by decreasing the amount of connecting pathways between surface features and/or decreasing the width and depth of the coating constituting those pathways.

Another way to measure the amount of conductive coating and/or ionic compound used, in order to minimize that amount, is by the amount of surface area that is actually covered. In regards to actual surface area coated, preferably, the surface area coated in conductive coating and/or ionic compound is less than 6 cm$^2$ for any one dry electrode. More preferably, the surface area coated in conductive coating and/or ionic compound is less than 5.5 cm$^2$. Still more preferably, the surface area coated in conductive coating and/or ionic compound is less than 5 cm$^2$. Yet more preferably, the surface area coated in conductive coating and/or ionic compound is less than 4.5 cm$^2$. Even more preferably, the surface area coated in conductive coating and/or ionic compound is less than 4 cm$^2$. More preferably still, the surface area coated in conductive coating and/or ionic compound is less than 3.5 cm$^2$. Yet more preferably, the surface area coated in conductive coating and/or ionic compound is less than 3 cm$^2$. Still yet more preferably, the surface area coated in conductive coating and/or ionic compound is less than 2.5 cm$^2$. Even still more preferably, the surface area coated in conductive coating and/or ionic compound is less than 2 cm$^2$. Even still yet more preferably, the surface area coated in conductive coating and/or ionic compound is less than 1.5 cm$^2$. Still even more preferably, the surface area coated in conductive coating and/or ionic compound is less than 1 cm$^2$. Even still yet more preferably, the surface area coated in conductive coating and/or ionic compound is less than 0.75 cm$^2$. Still even more preferably yet, the surface area coated in conductive coating and/or ionic compound is less than 0.5 cm$^2$ for any one dry electrode.

In both varieties of embodiments of the above described monolithic dry electrodes, the minimized area of conductive coating and/or ionic compound on the lower surface of the device must comprise a continuous pathway of the coating from that coated area to and around the edge of the encouragement lip to the upper surface of the device, and to the connector located on said upper surface. Such continuous pathway allows the biopotential signals to be transmitted from the subject to the monitoring equipment in spite of the use of a non-conductive dry electrode body and a preferably minimized amount of conductive coating and/or ionic compound. This continuous pathway may be created by providing a strip-like path of the conductive coating and/or ionic compound from the portion of the lower surface out from the center of the lower surface towards the edge of the device, around the edge of the device thus connecting the lower surface to the upper surface, and then to the center of the upper surface of the device and to the connector. In some embodiments, multiple such strips are provided to ensure a strong, secure electrical pathway from the surface features to the connector and to the monitoring equipment, for example in case one pathway becomes damaged, rubs away, or is otherwise broken. However, preferably, only a single pathway of connective coating is provided, and is applied in a manner and with properties so as to ensure a continuous electrical connection and pathway.

The dry electrode can be formed from a variety of materials and processes known to those skilled in the art. The substrate from which the surface features are formed or to which they are added can, by way of example but not limitation, be made from the following: a conductive metal sheet, where such conductive metals include, but are not limited to, stainless steel, nickel, copper, aluminum, and the like; a semi-conductive material, including, for example, silicon and doped silicon wafers; ceramics, including, for example, oxides; polymers, including, for example, electrically conductive polymers such as polyimides; and other varieties of plastics. Preferably, all non-conductive substrates are coated, such as with Ag/AgCl, or doped to make the substrate semi-conductive or conductive. There are in general four processes by which embodiments of the dry electrodes of the present invention are preferably manufactured: injection molding, casting or depositing; replication; micro-machining; or stamping or pressing from a sheet of metal, polymer sheet or polymer powders.

It is understood that the dry electrodes of the present invention may have a combination of the various surface features described throughout this application. Various features of the present invention are described within this patent application. It is understood that the present invention can be considered to embody many of these features in various combinations without departing from the spirit of the present invention. A small number of examples of the present invention are described in the following embodiments. Various features and functions of the present invention are discussed in greater detail in U.S. Pat. Nos. 6,782,283, 6,785,569, 7,032,301, 7,286,864, 7,489,959, and 8,201,330, and U.S. patent application Ser. No. 13/826,185, all of which disclosures are incorporated by reference into the present application.

As described earlier, the dry electrode of the present invention comprises an upper and a lower surface. The lower surface can take many forms. For instance, the lower surface can be flat, concave, convex, or some other unique shape. The dry electrode can be substantially flat on its lower surface. Various embodiments of the present invention could include changes in the dry electrode's lower surface. Whether the lower surface is perpendicular to the dry electrode's vertical axis or sloped depends on the application. The dry electrode can also be substantially concave on its lower surface. An example is where the lower surface is outwardly curved like a portion of the inner surface of a large sphere. The dry electrode can also have a convex shape on its lower surface. An example is where the lower surface curves or bulges outward, like a portion of the exterior surface of a large sphere. The lower surface of the dry electrode is not limited to one of the aforementioned shapes, and may take on a number of other unique shapes or some combination of the shapes listed above. Preferably, the dry electrode is molded or shaped to match the shape of the wearable into which it is incorporated; thus, the lower surface might be convex for an earbud and slightly concave for a hat, helmet, or sweatband.

As discussed above, the lower surface of the dry electrode of the present invention may further include a number of surface features for displacing, cracking, or perturbing the stratum corneum or outer layer of the epidermis and accessing the lower layers of the epidermis. Such displacing, cracking, or perturbing of the skin may include the surface features physically penetrating the stratum corneum and accessing and physically contacting the lower layers of the skin. However, it may be preferable for the surface features to merely perturb, stretch, or open the stratum corneum by cracking or displacing it without actually physically penetrating it, in order to provide a lower electrical resistance pathway from the lower layers of the skin to the dry electrode. Penetrating surface features can take many shapes including but not limited to pyramidal, needle-like, triangular, or any other shape that can be tapered to a point or tip. Where the surface features are penetrating, preferably, the size and shape of the penetrator is such that the penetrator(s) will not break or bend during normal use, will limit the depth the penetrator enters the skin under typical application conditions, and/or will anchor the device to prevent motion artifacts or any substantial movement. Such penetrating surface features are explained in detail in U.S. Pat. No. 6,785,569 to Schmidt et al., which is incorporated by reference.

A ridge as a surface feature of a dry electrode is preferably a long, narrow structure or elevation. The ridge(s) can have a variety of cross sections over a length. Examples of these cross sections include, but are not limited to, a square, rectangle or trapezoid, a pointed surface like that of a triangle, a domed surface like that of an arch or arc, a cross section with a concave surface between to ridge lines forming the two ridge lines, some other unique cross-section or the like. The cross section of the ridge extends for a length. The length of the ridge is preferably substantially longer than the height or width of the cross-section of the ridge. The surface of the ridge away from the substrate, when applied to the skin surface, depresses, but does not need to penetrate the skin but anchors the device in place to prevent motion artifacts, to displace hair, dead skin cells and/or detritus, to increase the surface area of the device in contact with the skin, and to be capable, in part, of transmitting an electric potential which can be measured from the surface of the skin through the ridge.

A column is another type of structure or elevation that can be used as a surface feature of the dry electrode of the present invention. A column can have a variety of cross sections over a length. Examples of these cross sections include, but are not limited to, a square, rectangle or trapezoid, a pointed surface like that of a triangle, a domed surface like that of an arch or arc, a cross section with a concave surface between two points (wherein the distance from the base to either point is greatest height of the column for the cross-section), some other unique cross-section or the like. The cross section of the column like a ridge extends for a length. However, the width of the column is preferably in proportion to the height of the cross-section of the column, and more preferably shorter than the height of the column. The surface of the column away from the substrate, when applied to the skin surface, depresses, and does not easily penetrate the skin but anchors the device in place to prevent motion artifacts, to displace hair, dead skin cells and/or detritus, to increase the surface area of the device in contact with the skin, and to be capable, in part, of transmitting an electric potential which can be measured from the skin through the ridge.

A penetrator is another surface feature that can be used in the dry electrode of the present invention. The penetrator is sized and shaped for displacing, cracking, or perturbing the stratum corneum or outer layer of the epidermis, and accessing the lower layers of the epidermis. The penetrator can take many shapes, including, but not limited to, pyramidal, needle-like, triangular, or any other shape that can be tapered to a point or tip. The surface of the penetrator away from the substrate, when applied to the skin surface, readily penetrates the skin, preferably anchors the device in place to prevent motion artifacts or any substantial movement, increases the surface area of the device in contact with the skin and lower layers of the epidermis, and is capable, in part, of transmitting an electric potential which can be measured from the skin and lower layers of the epidermis through the penetrator.

The epidermal stop, which can be used in the present invention, is a structure or elevation. Epidermal stops are structures of a particular height with respect to the height of the penetrator(s) or other surface features so as to prevent the penetrator(s) or other surface features such as columns and ridges from penetrating into the dermis of the skin or unduly distorting the surface of the skin, respectively, where they might cause discomfort to the subject. Epidermal stops may also be incorporated into a penetrator, ridge, column or like surface feature or can be a separate surface feature. The epidermal stops may, however, have any shape known to those skilled in the art that would effectively prevent the penetrator(s) from entering the dermis of the skin, or from being applied to deeply. The epidermal stops are preferably applied in an array among the penetrators, therefore further minimizing inadvertent deep penetration or over penetration by the penetrator(s) or minimizing significant distortion of the skin by other surface structures. If the epidermal stop is a separate surface feature or incorporated into another structure, preferably, the epidermal stop in combination with at least one other surface feature or two structures with incorporated epidermal stops create a detritus trough.

A detritus trough is the area interposed between adjacent surface structures or features. These troughs, when provided or naturally occurring in the design, allow for a more accurate placement of the surface features by allowing for displacement of the hair and other detritus on the skin in these troughs. Preferably, the detritus troughs are sufficient in number and size to allow for placement of the device on skin with a significant amount of hair such as for example the scalp or the chest of a male subject. Detritus troughs are created to maximize the area available for optimal device to skin contact, by improving the probability that hair and other detritus will enter the troughs and not preventing the surface features from either coming in contact with the skin or penetrating the skin. Thus detritus troughs may be parallel to one another, perpendicular to one another, or in any other orientation made to improve the contact of the device with the skin of the subject.

An anchor, which can be used in the present invention, is a structure or elevation that stabilizes the physiological device against a subject's skin. This stabilization further preferably prevents motion artifacts in the electrophysiological signal from the device, or any substantial movement. While the anchor can also be any of the structures described above, the anchor may also serve no other purpose except to stabilize or reduce movement of the device on the subject's skin. The anchor(s) can have a variety of cross sections over a length as described above for the various surface structures.

The ridges, columns and penetrators also increase the amount of surface area of the skin in contact with the dry electrode, which is applied. This allows for greater pick up of (or stronger) signals from the skin's surface, and further allows for the dry electrode to be better anchored to the subject's skin resulting in less artifacts to the signal through movement and the like. The electric voltage from these surface features is measured using conventional measuring devices.

As discussed earlier, the dry electrode further comprises an upper surface, which is the surface that faces away from the subject when the dry electrode is applied to the subject. In some embodiments, the upper surface may comprise some variety of connector used to connect the dry electrode to monitoring equipment, and to complete an electrical pathway from the lower layers of the subject's skin to said monitoring equipment. The connector may be of any variety commonly known to those of skill in the art currently, or later developed. Examples of such connectors include, but are not limited to, snap connectors, button connectors, tension or compression fittings, and the like.

As discussed previously, an independent, separate encouragement ring, to which an independent electrode component can be attached, may be provided. The independent, separate encouragement ring comprises an opening in its center with a diameter equal to that of an independent, separate recording portion, preferably comprising surface features. The opening allows the recording portion to be placed inside of the encouragement ring's opening, and allows the encouragement ring to surround and hold the recording portion. The independent recording portion may attach to the opening of the encouragement ring by threads, a locking system, thermal compression, or like techniques. When the separate encouragement ring and recording portions are combined together, they form a single dry electrode as described above, comprising an upper and a lower surface. The separate encouragement ring preferably curves up, away from the subject's skin when applied, such that, when viewed from the lower surface, the dry electrode has a convex shape. This encouragement ring provides stability to the dry electrode such that when the device is placed on a subject's skin, the ring encourages the device to become seated in contact with the subject's skin and to minimize movement of the device. This helps to increase signal quality and efficacy while minimizing artifacts in the physiological signal being acquired. Additionally, the encouragement ring provides increased surface area to the upper surface of the dry electrode which allows the device to be combined with an adhesive collar or some wearable or garment to be applied to the subject's skin in a more stable and secure fashion.

The use of a separate encouragement ring provides advantages such as allowing for the dry electrode to be manufactured using different materials for its different portions (i.e., separate encouragement ring and recording portions). The use of different materials for the different portions of the electrode provides benefits both in the manufacture and use. With respect to manufacturing, the separate encouragement ring may be constructed of a less expensive material, such as various low cost of plastics known to those skilled in the art. Thus, the entire separate encouragement ring, which constitutes a significant portion of the entire assembled recording device, may be made from a material, and by a process that reduces manufacturing costs, and therefore helps reduce overall cost of the electrode. Further, the separate encouragement ring allows for the amount of conductive coating and/or ionic compound required to be minimized by creating an electrical pathway between the two separate portions, rather than all the way out and around the edge of the encouragement ring. These cost-cutting features particularly provide an advantage over existing dry electrodes which are known to those skilled in the art to be expensive to produce due to the use of expensive conductive materials, or the need to completely cover the electrode in an expensive conductive coating and/or ionic compound such as Ag/AgCl.

In addition to reducing costs of the device, using a separate encouragement ring allows the encouragement ring and the recording portion to be constructed of materials that have different properties to provide different features to the device. For example, the recording portion is preferably constructed of a material that has electrical conductive properties and electrical impedance properties that are conducive to transmitting biopotential signals from the subject to the monitoring equipment, or alternatively (or additionally) may be a non-conductive material that is coated in a conductive layer such as Ag/AgCl to reduce the impedance, provide an electrical pathway, and provide a redox reaction promoting the flow of ions and thus allowing for better signal transmission. However, the encouragement ring being constructed of a different material allows the ring to provide additional characteristics, features, or properties to the device when assembled. The separate encouragement ring may be constructed of a material with a particular stiffness which helps anchor the device more securely to the subject's skin. Particular levels of flexibility may also be achieved with the encouragement ring, allowing the device to be situated on a curvier or less regularly-shaped part of the body while still providing the function of situating the recording portion in secure contact with the subject's skin. The encouragement ring material can be chosen based on any number of such desired features or characteristics, and still provide the reduction in cost while maintaining the secure fit of the electrode to the body. The end result of providing a separate encouragement ring constructed of a different material is that the function of the encouragement ring, to provide anchoring of the device to the subject's skin, can be optimized to better situate or apply the device in different locations of the body. Different materials yield different properties in the encouragement ring, and thus provide the applicable biasing forces causing the device to anchor to the skin, differently in different locations. Some encouragement rings may be adapted to affix the device to hairy regions of the body, or to curvier regions. Having separate encouragement rings allows the device to be applied in many different locations and fashions, while still providing the required biasing forces to the subject's skin to drive the device down into the skin, and more securely anchor the device thereto. In some embodiments this ensures a higher quality signal is transmitted from the subject to the monitoring equipment, and further minimizes artifacts and noise within the signal. The separate encouragement ring may be attached to the electrode or recording portion by any means currently known to those in the art or later developed, including, but not limited to, threads, compression, clips or other mechanical fixture methods, adhesives, and the like.

Other embodiments of the present invention do not include a separate encouragement ring. In such embodiments, the dry electrode is made from a single piece of material, and in some embodiments it preferably comprises a lip extending radially outward and curving upward away from the lower surface of the recording device, surrounding and providing an edge for a stamped or molded sheet metal or plastic piece. This lip provides the same function and utility as the separate encouragement ring described above, but is part of a unitary construction of the dry electrode, rather than being a separate piece that is later attached to a separate recording portion. The lip comprises the edge or near-edge portion of the dry electrode, and the lip is herein preferably defined as the portion where the lower surface of the dry electrode begins to curve upward to the edge or near edge of the dry electrode.

The distance of the curved lip portion is herein defined as the distance of curvature of the lip. The same distance of curvature definition applies to the curved portion of the separate encouragement ring in embodiments comprising a separate encouragement ring. The curvature of the lip or encouragement ring may be wholly contained in the lip or encouragement ring portion, or may begin in the lower surface of the recording portion of the device itself. That is, the lower surface itself need not be entirely flat, but may gradually curve up into the lip or encouragement ring. Many embodiments are envisioned with both constructions: either with a flat area between the lower surface where the surface features are located and where the lip or encouragement ring begins, or where the lower surface itself begins to curve up and meet the curvature of the lip or encouragement ring to form an essentially smooth curve. In all embodiments having such a design, preferably, the distance of curvature of the lip or separate encouragement ring is greater than 0.2 cm. More preferably, the distance of curvature of the lip or separate encouragement ring is greater than 0.25 cm. Still more preferably, the distance of curvature of the lip or separate encouragement ring is greater than 0.3 cm. Yet more preferably, the distance of curvature of the lip or separate encouragement ring is greater than 0.4 cm. Even more preferably, the distance of curvature of the lip or separate encouragement ring is greater than 0.45 cm. Still yet more preferably, the distance of curvature of the lip or separate encouragement ring is greater than 0.5 cm. Still even more preferably the distance of curvature of the lip or separate encouragement ring is greater than 0.6 cm. Yet still more preferably, the distance of curvature of the lip or separate encouragement ring is greater than 0.75 cm. Yet even more preferably, the distance of curvature of the lip or separate encouragement ring is greater than 1.0 cm. Even yet more preferably, the distance of curvature of the lip or separate encouragement ring is greater than 1.5 cm. Most preferably, the distance of curvature of the lip or separate encouragement ring is greater than 2.0 cm.

The lip, by its very nature, has a radius of curvature which defines the rate at which the lip curves upward from the lower surface of the dry electrode. It is to be understood that the entire lip or encouragement ring does not need to have the same or constant radius of curvature along the entire distance of curvature. In other words, it is important to note that the radius of curvature may change along the length of the distance of curvature. Preferably, the radius of curvature of the lip or encouragement ring over substantially all of the distance of curvature is greater than 0.5 cm. More preferably, the radius of curvature of the lip or encouragement ring over substantially all of the distance of curvature is greater than 0.75 cm. Still more preferably, the radius of curvature of the lip or encouragement ring over substantially all of the distance of curvature is greater than 1.0 cm. Yet more preferably, the radius of curvature of the lip or encourage- ment ring over substantially all of the distance of curvature is greater than 1.125 cm. Even more preferably, the radius of curvature of the lip or encouragement ring over substantially all of the distance of curvature is greater than 1.25 cm. More preferably still, the radius of curvature of the lip or encouragement ring over substantially all of the distance of curvature is greater than 1.5 cm. Yet more preferably still, the radius of curvature of the lip or encouragement ring over substantially all of the distance of curvature is greater than 1.75 cm. Still even more preferably, the radius of curvature of the lip or encouragement ring over substantially all of the distance of curvature is greater than 2.0 cm. Even still more preferably, the radius of curvature of the lip or encouragement ring over substantially all of the distance of curvature is greater than 2.5 cm.

It should be noted that not all embodiments will utilize encouragement rings or curved lip portions in the dry electrode; in many embodiments, such as ear bud embodiments, the dry electrode will be integrated into the wearable without such features.

Body Temperature Sensors.

Many embodiments of the present invention further include sensors for measuring the subject's body temperature. Because body temperature affects the rate of chemical reactions critical to normal body operation and healthy survival, the body's thermoregulation mechanisms attempt to keep the subject at optimum operating temperature, 37° C. (98.6° F.) on average in humans, with variation among individuals and in accordance with seasonal, hormonal and menstrual cycles and circadian rhythms—with about 0.5° C. (0.9° F.) variance between daily high and low points. Increased body temperature is indicative of strenuous physical activity, and body temperature change—whether severely increased or severely decreased—is also symptomatic of illness or other dangerous conditions such as hypothermia. Eating, drinking, and smoking can all influence body temperature, as can sleep disturbances (with temperature dropping during rest). Thus, monitoring of body temperature can provide useful exercise and health information, and can alert the subject to take a break from exercise, to oncoming sickness, to bedtime or waketime, to mealtime or caloric restriction, to periods of fertility, etc. It is also believed that an increase in daily body temperature variation can provide an indicator of increased overall physical fitness.

Body temperature may also vary based on measurement methods and particularly the placement of the measurement sensor. Among healthy adults, typical daytime temperatures are about 37.5° C. (99.5° F.) for rectal, vaginal, or otic measurements; about 36.8° C. (98.2° F.) for oral measurements; and about 36.5° C. (97.7° F.) for axillary measurements under the armpit. Although different sensor placements may yield different measurements, measurements from different points tend to be correlated, thus the temperature at one point can be estimated or predicted with measurement from another point; however, axillary, otic, and other skin-based temperatures may sometimes correlate poorly with core body temperature, and skin-based temperatures are more variable than other measurement sites as the body uses the skin as a cooling device. Resultantly, skin temperatures are more influenced by ambient temperatures than core temperatures are. Preferably, temperature is measured at multiple sites and the acquired measurements are algorithmically combined using methods such as weighted averages to yield more accurate temperature readings.

For head-worn or head-based systems such as the present invention, there are several viable options for measuring the subject's body temperature, including orally, otically, from the forehead, or from the superficial temporal artery. The preferred methods and sensors used to measure body temperature vary based on the particular embodiment. For example, a cap or hat embodiment may readily use sensors that measure the temperature from the subject's forehead, but an embodiment of headphones would more readily benefit from a temperature sensor in the ear (tympanic) or over the superficial temporal artery. The superficial temporal artery is a major artery located in the head that arises from the external carotid artery when the external carotid bifurcates and separates into the superficial temporal artery and the maxillary artery. The superficial carotid artery exhibits a palpable pulse detectable superior to the zygomatic arch, anterior and superior to the tragus, and is located close to the surface of the skin in most subjects, and thus offers an accurate, accessible and efficacious source for measuring the subject's body temperature, as long as the subject's flow of blood is permanent and regular. Such sensors can be of any variety capable of sensing and measuring temperature transcutaneously. Otic and forehead body temperature sensors typically use infrared sensors, by, for example, shining an infrared light off the tympanic membrane. Thermistors and thermocouples can in some cases also be used to acquire body temperature measurements.

Galvanic Skin Response Sensors.

Galvanic skin response sensors measure a subject's level of excitement, stress, or other such indicators of psychological or physiological stimulation or arousal, as a function of the increased skin conductance caused by the increase in sweat. Skin conductance is a measure of the electrical conductance of the skin, and is commonly known in the art as one of several names, including galvanic skin response (GSR), electrodermal response (EDR), psychogalvanic reflex (PGR), skin conductance response (SCR) or skin conductance level (SCL). Galvanic skin response typically varies based on the moisture level of the subject's skin, such as is caused by sweating. Galvanic skin response may measure stimulation or arousal due to the fact that sweat is controlled by the sympathetic nervous system, which is the part of the autonomic nervous system that initiates or activates the fight-or-flight response to some stimulus applied to the sympathetic neurons.

Galvanic skin response sensors measure the recorded electrical resistance between two electrodes when a very weak current is steadily passed between them. The sensors are normally placed a short distance apart, and the resistance recorded varies in accordance with the emotional state of the subject. Galvanic skin potential (GSP) refers to the voltage measured between two electrodes without any externally applied current, and is measured by connecting the electrodes to a voltage amplifier. Similarly, this voltage varies with the emotional state of the subject. Galvanic skin response can be highly sensitive to emotions in some people, though the GSR measurement cannot differentiate between what emotions are causing the response. GSR measurements are typically very small, such as on a microsiemen scale, but an accurately and correctly calibrated sensor and signal acquisition device or electronics can readily ascertain and measure such small values and changes in the GSR on such a scale. Because the fight-or-flight response, activated by the release of noradrenaline and adrenaline, also results in increased heart rate, a correlation between increased electrical conductance of the skin (as measured by a GSR sensor) and increased heart rate (as measured by a heart rate sensor such as an ECG sensor or an IR/optical sensor) can provide an especially good indicator of excitement/stress.

Pulse Oximetry Sensors.

Another example of the sensors that may be used in conjunction with the present invention include the use of a pulse oximeter. Pulse oximeters of any type known to those skilled in the art may be used. Generally, depending on the location of attachment to the subject's body, pulse oximeters tend to be either transmission or back scatter (reflection) sensors. Transmission sensors operate by generating a source of light at a known frequency and wavelength, passing said light through the subject's body, and measuring the amount of light that exits the subject's body on the other side. Transmission sensors, and particularly pulse oximeters, are typically applied fingertips, the nose, or earlobe, due to the thinness of those parts of the body and the ease in applying a sensor to both sides thus enabling the transmission measurement. On other areas of the body that do not lend themselves as well to applying such sensors, and back scatter or reflection sensors may be used. Back scatter sensors operate by generating a source of light at a known frequency and wavelength, and then measuring the amount of light that bounces or reflects back to the measurement sensor which is on the same side as the light generator. These sensors tend to be less accurate than transmission sensors due to the loss of light as it scatters once it enters the subject's body; 100% reflection is generally unachievable. In spite of the generally decreased accuracy, these sensors, particularly in pulse oximeters, are useful for application to the subject's ear to which would be uncomfortable and difficult to apply a transmission sensor. More specifically, with regard to the preferred sensor, the pulse oximeter can measure the oxygenation of the subject's blood by producing a source of light originating from the oximeter at two wavelengths (such as, in one embodiment, 650 nm and 805 nm). The light is partly absorbed by hemoglobin, by amounts which differ depending on whether it is saturated or desaturated with oxygen. By calculating the absorption at the two wavelengths the proportion of hemoglobin which is oxygenated can be estimated. Some embodiments, where the optional pulse oximeter is attached to or incorporated into a helmet, may be referred to as helmet-mounted pulse oximeter (HMPO) embodiments. In some embodiments, a pulse oximeter may be placed on a subject's fingertip. In other embodiments, a pulse oximeter may be placed directly on a subject's earlobe or forehead. In yet other embodiments, a pulse oximeter may be incorporated into a mask, helmet, or some other wearable, and then placed on the subject's forehead or earlobe when the mask, helmet or wearable is donned. In still yet other embodiments, a pulse oximeter may be attached in the subject's ear cup. In yet other embodiments, a pulse oximeter may be incorporated into a mask, helmet, or some other wearable, and is then placed in the subject's ear cup. In even other embodiments, a pulse oximeter may be applied to the bridge of the subject's nose, and is preferably incorporated into a mask, helmet, or other wearable.

Near Infrared Sensors.

Near-infrared (NIR) sensors may be included in many embodiments of the present invention. An example of an application for near-infrared measurements is for pulse oximetry and measurement of blood oxygen concentration. The primary application of NIRS to the human body uses the fact that the transmission and absorption of NIR light in human body tissues contains information about hemoglobin concentration changes. When a specific area of the brain is activated, the localized blood volume in that area changes quickly. Optical imaging can measure the location and activity of specific regions of the brain by continuously monitoring blood hemoglobin levels through the determination of optical absorption coefficients.

NIRS can be used for non-invasive assessment of brain function through the intact skull in human subjects by detecting changes in blood hemoglobin concentrations associated with neural activity, e.g., in branches of cognitive psychology as a partial replacement for functional Magnetic Resonance Imaging (fMRI) techniques. NIRS can be used on infants, and NIRS is much more portable than fMRI machines, even wireless instrumentation is available, which enables investigations in freely moving subjects. However, NIRS cannot fully replace fMRI because it can only be used to scan cortical tissue, where fMRI can be used to measure activation throughout the brain. Special public domain statistical toolboxes for analysis of stand alone and combined NIRS/MRI measurement have been developed (NIRS-SPM).

The application in functional mapping of the human cortex is called diffuse optical tomography (DOT), near-infrared imaging (NIRI) or functional NIRS (fNIR). The term diffuse optical tomography is used for three-dimensional NIRS. The terms NIRS, NIRI, and DOT are often used interchangeably, but they have some distinctions. The most important difference between NIRS and DOT/NIRI is that DOT/NIRI is used mainly to detect changes in optical properties of tissue simultaneously from multiple measurement points and display the results in the form of a map or image over a specific area, whereas NIRS provides quantitative data in absolute terms on up to a few specific points. The latter is also used to investigate other tissues such as, e.g., muscle, breast and tumors. NIRS can be used to quantify blood flow, blood volume, oxygen consumption, reoxygenation rates and muscle recovery time in muscle.

By employing several wavelengths and time resolved (frequency or time domain) and/or spatially resolved methods blood flow, volume and absolute tissue saturation ($StO_2$ or Tissue Saturation Index (TSI)) can be quantified. Applications of oximetry by NIRS methods include neuroscience, ergonomics, rehabilitation, brain computer interface, urology, the detection of illnesses that affect the blood circulation (e.g., peripheral vascular disease), the detection and assessment of breast tumors, and the optimization of training in sports medicine.

The use of NIRS in conjunction with a bolus injection of indocyanine green (ICG) has been used to measure cerebral blood flow and cerebral metabolic rate of oxygen consumption. It has also been shown that CMRO2 can be calculated with combined NIRS/MRI measurements.

NIRS is starting to be used in pediatric critical care, to help deal with cardiac surgery post-op. Indeed, NIRS is able to measure venous oxygen saturation ($SVO_2$), which is determined by the cardiac output, as well as other parameters ($FiO_2$, hemoglobin, oxygen uptake). Therefore, following the NIRS gives critical care physicians a notion of the cardiac output. NIRS is liked by patients, because it is non-invasive, is painless, and uses non-ionizing radiation.

Optical Coherence Tomography (OCT) is another NIR medical imaging technique capable of 3D imaging with high resolution on par with low-power microscopy. Using optical coherence to measure photon path length allows OCT to build images of live tissue and clear examinations of tissue morphology. Due to technique differences OCT is limited to imaging 1-2 mm below tissue surfaces, but despite this limitation OCT has become an established medical imaging technique especially for imaging of the retina and anterior segments of the eye.

GPS Sensors.

Global positioning system (GPS) sensors may also be included on many embodiments of the present invention. GPS sensors are known in the art to be useful in tracking the subject's location, distance traveled, and speed. GPS measurements can also be combined with accelerometry measurements or other measurements of pedometry to gauge a subject's pace, defined as the average distance one foot travels from the point it leaves the ground until the same foot touches the ground again. Pace can be computed by dividing distance traveled over number of paces (i.e., the number of two-step sequences). Measurements from GPS or determinations based on GPS are useful for fitness and health applications wherein an athlete or person exercising can track his or her distance covered during exercise, and can be useful in other applications, for tracking similar values. For example, an Over the Road truck driver may use various embodiments of the present invention including a GPS sensor to monitor the distance traveled on a trip while monitoring the various other signals and measurements described herein, thus allowing for tracking of a particular shipment as well as providing messages or warnings to the driver when it is time to pull over and rest to improve the safety of the truck driver and other motorists on the road. This may be done with maximum efficiency because safe, legal, convenient, or otherwise appropriate places to pull over may be predefined in the GPS system, thus, a trucker will not be forced to pull over to rest in a place where it is unsafe, illegal, inconvenient, or otherwise inappropriate to do so. The GPS sensors of the present invention may additionally, in some optional embodiments, be able to provide altitude measurements as well, by utilizing a trilateration technique of synchronizing and measuring the distances between the system or device and at least four different satellites.

Accelerometers.

Accelerometers may be used to measure determine the subject's body position and orientation, g-forces, and provide other functions such as providing time synchronization with the subject's vehicle (e.g., aircraft). Such accelerometers may be of any type known to those skilled in the art, including magnitude accelerometers and 3-axis accelerometers. Preferably, the accelerometers are MEMS-based. Accelerometers are often included to detect high g-force conditions, angular movements and accelerations, and the like. The time synchronization feature primarily allows for post-mission (in military applications) or post-application review of data in which the subject's position and orientation, as well as g-forces experienced, are compared via time signature to known events or occurrences detected by other sensing systems, or other sensors on the same device. This helps to align data points in order to allow and facilitate analysis of what circumstances may lead to or cause the onset of dangerous conditions, episodes or events in order to help develop new preventative, mitigating, or treatment systems and methods. Accelerometry data can also be used to derive pedometric data because the recorded shock of landing on a foot is indicative of a taken step. In combination with GPS data or other data indicative of distance traveled, this pedometric data can yield stride, a useful metric for walkers and runners.

Gyroscopes.

Another type of sensor included in many embodiments of the present invention includes gyroscopes. Gyroscopes are often used to measure, detect or otherwise determine orientation of the subject or the system or device. Preferably, electronic or MEMS-based gyroscopes are used. The gyroscopes of the present invention are preferably 3-axis gyroscopes, thus requiring only a single gyroscopic device to measure the angular momentum, and thus orientation, in all three dimensions or axes rather than using three separate gyroscopes where one measures each dimension or axis. The preferred characteristics aid in miniaturization and accuracy of the measurements of the system and devices, while also ensuring the most comfortable and enjoyable fit and experience for the user. Inclusion of gyroscopes in particular embodiments of the present invention, particularly in conjunction with accelerometers, allows the system and devices to detect and measure the subject's movement. Such measurements of movement aid in the tracking of health-related metrics and allow for a more robust and diverse set of data to be collected as well as derived.

The motion sensors (including accelerometers and gyroscopes) of the present invention can also be used in processing and filtering the data from other sensors, including electrophysiological and IR sensors, which tend to be sensitive to motion artifacts, using cancellation methods known in the art to assist in the attenuation and removal of motion artifacts from collected data.

Altimeters.

Altimeters are yet another type of sensor that may be included in various embodiments of the present invention. Altimeters are sensors that are able to detect and measure the altitude of the system or device, and thus the subject wearing, using or otherwise employing the system or device. A measure of altitude is particularly important for fitness applications to determine elevation climbed and/or descended during a workout routine, as when jogging through hilly terrain, mountain climbing, or ascending buildings.

As noted herein, some optional embodiments may provide altitude measurements using a GPS sensor as opposed to a separate, dedicated altimeter, where the GPS sensor uses a trilateration technique to measure the distance between the system or device and at least four different satellites. Also optionally, and particularly for applications in vehicles or aircraft, a radar altimeter or other such altimeters that require a reference signal to be sent out (e.g., phase radio-altimeters) may be used in order to provide more accurate and precise altitude measurements where the increased precision is beneficial. However, in most embodiments a traditional pressure altimeter is the preferred type. Pressure altimeters measure the atmospheric pressure surrounding the system, device or subject. Typically, pressure altimeters compare the ambient atmospheric pressure to the pressure at sea level, and thus give an altitude measurement that corresponds to a height above sea level. As is known in the art, the greater the altitude, the lower the pressure, and thus the altimeter measures the pressure and calculates the altitude according to this inverse relationship and in relation to the pressure at sea level. Altimeters, like most sensors, require calibration because the pressure measurement is greatly variable and reliant on many environmental factors such as, for example, absolute temperature, gravitational acceleration and molar mass of the air surrounding the sensor. Changes in air pressure directly and significantly affect the measurement provided by altimeters, and changes in the weather (e.g., approach of a cold or warm front) can result in large fluctuations in altitude measurement without actually changing altitude. One simple way of calibrating the altimeter is to connect to the Internet, preferably through a wireless connection, and receiving from a nearby weather station the sea level ambient air pressure. The same data may also be input manually, but automatic calibration is preferred. Pressure altimeters are one example of a specific type of ambient pressure sensor that may be included with various embodiments of the present invention, though other pressure sensors may be included as well. Piezoresistor-based barometers such as the STMicroelectronics LSP331AP, as incorporated in smartphones, are known in the art and are accurate enough to distinguish between different floors of a building. Another example of an inexpensive MEMS barometer is the Freescale Semiconductor MPL115A2.

Pressure Sensors.

Many embodiments of the present invention further employ at least one pressure sensor. Pressure sensors may be included and used to measure many different pressures relating to physiological or environmental attributes of the subject. For example, in some embodiments where the subject is utilizing a breathing system of some variety (e.g., pilot wearing a flight mask, diver, and the like) pressure sensors may be included inside a breathing mask to measure in-mask pressure. Pressure sensors may also be included in the subject's gear or clothing, for example a dive suit or a flight vest. Vest or gear or clothing pressure becomes particularly important with regard high altitude, low pressure environments, such as pilots, aircrew, spacecraft crew, and the like. Many embodiments of the present invention are designed to be used in very low pressure environments, such as those just listed. In such environments, pressurized gas is often delivered to the subject through such a facemask. In order to actually breathe said gas, the subject often requires clothing or gear (e.g., flight vest) to provide counterpressure against the lung pressure created by the pressurized gas delivery. Such counterpressure is absolutely necessary in environments above what is known as the Armstrong Line, which is approximately located an altitude of 12 miles above sea level (between 18,900 to 19,350 meters), and which represents the altitude above which atmospheric pressure is so low that humans absolutely require a pressurized environment to survive. The pressure gradient created by the pressurized environment is what allows the human lungs to perform their function and for breathing to occur. In other words, the required pressure gradient, which is the difference between lung pressure and absolute pressure around the subject, is supplemented or created by the clothing or gear in some embodiments. Thus, pressure sensors in the subject's gear or clothing in such environments allows the system to monitor the subject's breathing conditions and detect or predict if the pressure gradient is sufficient to allow healthy breathing.

Other pressure sensors may also be included to measure ambient pressure surrounding the subject. Preferably, pressure sensors used for measuring mask and/or vest or clothing pressure are gauge pressure sensors. Gauge pressure sensors, as known to those skilled in the art, are those in which the pressure of the desired space or area is referenced against ambient pressure, and the differential between the two spaces is measured. Thus, in the example of a pilot in flight, the sensor for measuring either mask pressure or vest pressure is preferably a gauge pressure sensor comprising at least two channels for air intake, one open to the pilot's mask or flight vest, and the other channel open to the ambient, in-cabin pressure surrounding the pilot. The differential between the mask or flight vest pressure and the ambient in-cabin pressure is measured to determine the mask or vest pressure. The same or similar sensors might be used to measure mask or clothing/gear pressure for other subjects as well, firefighters, first-responders, rotorcraft pilots and crew, other fixed wing aircraft crew, or any other subject utilizing such clothing, equipment or gear.

Still other pressure sensors may also be included. Many embodiments may comprise at least one pressure sensor for measuring ambient pressure separately from any user-related pressure. Such ambient pressure sensors may be used to separately measure cabin pressure (for aircraft and vehicles), ambient air pressure (for man-mounted systems utilized by subjects on the ground or in non-pressurized vehicle cabins, or for high altitude training or exercise purposes), ambient water pressure for divers, and the like. Typically, such sensors are absolute pressure sensors. Absolute pressure sensors are known to those skilled in the art to measure the differential between the measured atmospheric pressure and a sealed atmospheric channel within the sensor. Preferably, the sealed channel, or internal vacuum reference chamber, in the sensor is substantially set to about 1 atmosphere (atm), which is equal to about 1013.25 millibar (mbar). 1000 mbar is approximately the standard air pressure at sea level. Thus, the measured ambient pressure is compared against the sealed channel's set pressure, and the measured differential between the two is the absolute pressure surrounding the subject. In many embodiments, gauge pressure sensors and absolute pressure sensors may be used in conjunction with each other to create a more complete pressure profile for the user and his or her environment. Such pressure measurements can then be used, either alone or in conjunction with the measurements and recordings of the other sensors described herein, to help monitor the subject's status, to help detect and predict the onset of dangerous conditions, to mitigate or prevent the onset of such conditions and their symptoms by triggering a warning or alarm to the user or a third party, or triggering automated or semi-automated measures.

Pressure sensors used with the present invention preferably require low power, and are capable of operating accurately and repeatably in extreme conditions (e.g., high pressure, high temperature, low temperature, etc.). The preferred pressure sensors are piezoresistive in nature. Pressure sensors used in the present invention may be of virtually any type known to those skilled in the art (e.g., Honeywell TRUSTABILITY series pressure sensors). If such commercially available sensors are used, they are either altered or repackaged in a housing as described herein to become modular, and readily adaptable for use in the various breathing systems and environments for which the present invention is intended to be used. Such housings containing the sensors are then able to be attached to, combined with, or integrated into breathing systems either as part of the construction of said system, or as a retrofit onto an existing system. With regard to the environments in which such sensors are used, as is known to those skilled in the art, pressure decreases as altitude increases. Preferably, for ground or air applications, the pressure sensors used have an effective measurement range of at least +/−1000 mbar. More preferably, for ground or air applications, the pressure sensors used have an effective measurement range of at least +/−900 mbar. Still more preferably, for ground or air applications, the pressure sensors used have an effective measurement range of at least +/−800 mbar. Yet more preferably, for ground or air applications, the pressure sensors used have an effective measurement range of at least +/−700 mbar. Even more preferably, for ground or air applications, the pressure sensors used have an effective measurement range of least +/−600 mbar. Still yet more preferably, for ground or air applications, the pressure sensors used have an effective measurement range of least +/−500 mbar. Even yet more preferably, for ground or air applications, the pressure sensors used have an effective measurement range of least +/−400 mbar. Yet still more preferably, for ground or air applications, the pressure sensors used have an effective measurement range of least +/−300 mbar. Even still more preferably, for ground or air applications, the pressure sensors used have an effective measurement range of least +/−200 mbar. Most preferably, for ground or air applications, the pressure sensors used have an effective measurement range of at least +/−100 mbar.

Conversely, for underwater applications, pressure increases as the subject increases his or her depth, and thus pressure is measured differently than for air applications; however, these sensors still operate on the same principles. Preferably, for underwater applications, the pressure sensors used have an effective measurement range of least +/−1000 mbar. More preferably, for underwater applications, the pressure sensors used have an effective measurement range of least +/−2000 mbar. Still more preferably, for underwater applications, the pressure sensors used have an effective measurement range of least +/−4,000 mbar. Yet more preferably, for underwater applications, the pressure sensors used have an effective measurement range of least +/−8,000 mbar. Even more preferably, for underwater applications, the pressure sensors used have an effective measurement range of least +/−12,000 mbar. Still yet more preferably, for underwater applications, the pressure sensors used have an effective measurement range of least +/−16,000 mbar. Even yet more preferably, for underwater applications, the pressure sensors used have an effective measurement range of least +/−20,000 mbar. Yet still more preferably, for underwater applications, the pressure sensors used have an effective measurement range of least +/−25,000 mbar. Even still more preferably, for underwater applications, the pressure sensors used have an effective measurement range of least +/−30,000 mbar. Still even more preferably, for underwater applications, the pressure sensors used have an effective measurement range of least +/−35,000 mbar. Yet even more preferably, for underwater applications, the pressure sensors used have an effective measurement range of least +/−40,000 mbar. Still even yet more preferably, for underwater applications, the pressure sensors used have an effective measurement range of least +/−45,000 mbar. Even still yet more preferably, for underwater applications, the pressure sensors used have an effective measurement range of least +/−50,000 mbar. Yet still even more preferably, for underwater applications, the pressure sensors used have an effective measurement range of least +/−55,000 mbar. Even yet still more preferably, for underwater applications, the pressure sensors used have an effective measurement range of least +/−60,000 mbar. Most preferably, for underwater applications, the pressure sensors used have an effective measurement range of least +/−65,000 mbar.

Ambient Temperature Sensors.

The preferred temperature sensor is a typical thermistor known to those skilled in the art. However, innovative housings and deployment assemblies allow the temperature sensor to be placed in various locations to measure various temperatures of or surrounding the subject. One such housing for the temperature sensor is preferably adaptable to attach in-line with a breathing tube for airflow applications such as when attached to a breathing mask (e.g., for pilots and divers). In other words, when the temperature sensor is used to measure the temperature of a breathing mix of gases as it travels through the breathing tube towards the subject's breathing mask, the housing connects in-line with that breathing tube, thus placing the temperature sensor in the direct flow of the breathing mix. Such a breathing mix temperature sensor may be placed at the distal end of the breathing tube, or at the proximal end, thus effectively attaching to both the breathing tube and mask, or in series with the proximal end of the tube and other modular sensors. The housing may also be attached to the breathing mask on the exhaled breath side, thus measuring the temperature of the exhaled breath. Alternatively, temperature sensors may be placed in any combination of these locations, thus measuring the temperature of the breathing mix, inhaled breath, and/or exhaled breath in any combination. Additionally, temperature sensors of any variety known to those of skill in the art may be included to measure ambient temperature of the environment surrounding the subject. Ambient temperature sensors are particularly useful and important for underwater, and more particularly diver, applications where the temperature of the surrounding water may have a significant and immediate impact on the subject's core body temperature, metabolic rate, and overall health condition.

Additional temperature sensors as described, or other varieties of temperature sensors known to those skilled in the art, may be included to measure various other temperatures related to the subject and the surrounding environment. Thus, in addition to inhaled and exhaled breath temperatures, other temperatures may be measured as well. A direct measurement of the subject's core body temperature may be taken, or may be calculated based on the inhaled and/or exhaled breath temperatures. Interior ambient temperatures may be measured in cabin, cockpit, or other such vehicle-employed systems, as well as exterior ambient temperatures, or those outside of the cabin, cockpit, or the like. For diving applications, temperature sensors may be included to measure ambient water temperature. In other words, temperature sensors may be included to measure the temperature of all gases inhaled or exhaled by the subject, as well as any environmental or ambient temperatures surrounding the subject, such that the conditions surrounding the subject may be known and used to help monitor the subject's and system's statuses, as well as to detect or predict and mitigate or treat dangerous breathing conditions, and to help alert the subject or third party.

Proximity Sensors.

Yet another type of sensor included in some embodiments of the present invention is a proximity sensor. Proximity sensors are used to detect the presence of nearby objects. Typically, proximity sensors emit an electromagnetic field or a beam of electromagnetic radiation (e.g., infrared), and look for changes in the field or return signal. The object being sensed is often referred to as the proximity sensor's target. Different proximity sensor targets demand different sensors. For example, a capacitive photoelectric sensor might be suitable for a plastic target; an inductive proximity sensor is suitable for a metal target. The maximum distance that this sensor can detect defines its "nominal range." Some sensors have adjustments of the nominal range or means to report a graduated detection distance. Proximity sensors can have a high reliability and long functional life because of the absence of mechanical parts and lack of physical contact between sensor and the sensed object. Various types of proximity sensors are known in the art, and the present invention could utilize any of the known types in various embodiments. Several of such varieties of proximity sensors include, but are not limited to, capacitive sensors, capacitive displacement sensors, Doppler effect sensors, inductive sensors, magnetic sensors, passive optical sensors, passive thermal infrared sensors, photocell or reflective sensors, ultrasonic sensors, and the like.

Audio Sensors.

Audio sensors, such as microphones or auscultatory sensors, may be integrated into the present invention to provide control input from the subject, to collect data from the subject, or to acquire ambient sound that is not recorded or collected but that may be passed through to the subject. For example, many forms of headphones and earbuds have noise cancelling features that operate by listening to sounds from the ambient environment and canceling out those sounds by introducing inverse sound waves to the listener. However, there may be times, as when jogging, driving, or riding a bicycle in traffic, that a subject may prefer to have ambient sounds more transparently passed through without being attenuated by noise cancellation. In such case, ambient audio microphones may pick up the ambient sounds and either pass them through without cancellation, or provide some intermediate measure of cancellation or transparency based on a user's preference as set through a user interface. Alternatively or in addition, certain ambient sounds may be selectively passed through based on their characteristics, such as frequency or tone, or their similarity to known noises. Thus, the device of the present invention could smartly and selectively pass through doorbells, telephone rings, fire or theft alarms, emergency vehicle sirens, car horns, screams, intelligible shouts, sounds of babies crying, and other alarming sounds, while smartly cancelling other noises that are less likely to be intended to alarm or alert the subject.

Preferably, in some embodiments the subject is provided with a user interface by which he or she may adjust the level of noise cancellation, ranging from complete external sound inclusion, incrementally or on a continuum up to more or less complete ambient noise isolation. In other embodiments the subject is provided with a user interface by which he or she may select, by characteristic, which types of sounds he or she would like to have passed through more transparently, and which sounds he or she would like attenuated by cancellation.

In addition to or instead of an ambient audio sensor, some embodiments of the present invention may incorporate an ear bone microphone capable of picking up the speech of the subject through an earbud, advantageously allowing for hands-free two-way communication.

Video Sensors.

Video sensors, such as cameras, video cameras, electro-optical infrared camera combinations, or the like, may be included as a sensor of various embodiments of the present invention as well. Video sensors of any variety can be used in conjunction with the present invention to provide or assist in proximity detection (e.g., recognize when certain embodiments of the device are brought close to the subject's face or donned upon the subject), record pictures or video of the user and/or his or her surroundings while the system or device is in use, to provide movement or motion recognition (e.g., detect a subject's eye movement and adapt output or display of information based on such eye movement), or other such uses for photographic or video data recorded by such sensors.

Eye Tracking Sensors.

Eye tracking sensors may be mounted on headgear (e.g., eyewear, the brims of hats, or in helmets) or may be placed on a separate device such as a display, smartphone or other portable electronic device, or on a dashboard or other vehicle or equipment control console. A basic eye tracking sensor may consist of only a single video camera which is able to determine, to within an acceptable degree of accuracy, where the eye(s) of a subject is/are looking, by, for example using an image matching algorithm or neural net algorithm to determine if eyes are pointed straight toward the camera or at some angle away from the camera. In certain applications it may be acceptable for such sensor to be only sensitive enough to make a binary determination (e.g., to determine only whether or not the subject has his or her eyes on the road, and thus to keep statistics of the amount of time the eyes are on the road and from such statistics make a determination of distracted or drowsy driving). More sophisticated versions of eye tracking sensors use two video cameras and an infrared light source and rely on a three-dimensional physiological model of the human eye. Infrared light from the IR source reflects off the pupil and cornea of the subject and is then captured by the two camera sensors. The collected images are processed to ascertain the position of the eye and the direction of the gaze with higher accuracy. Eye tracking can be used not only to collect data, but for data manipulation, user interface navigation, and control of the device(s) of the present invention, as well as for user identity recognition.

Eye tracking can also be done, to a limited degree, using data from EOG sensors.

Time Sensors.

Time is an important measurement in many fitness routine or activities and in many other occupational tasks. For example, it may be important to know how long a jogger has been jogging in order to compute the jogger's speed statistics, or how long a truck driver has been driving in order to provide notifications or warnings that it may be time for a rest. Methods of keeping time, for example in digital watch devices using an oscillating crystal such as quartz, are known in the art. Time can also be ascertained or synchronized by connecting to an Internet time server. In some embodiments of the present invention, preferably, the system or device of the present invention automatically detects when an exercise routine or activity or occupational task has begun and automatically begins timing the routine. For example, through analysis of collected motion sensor and/or GPS data, it can be determined that a subject has woken up, set out on a run, begun a bicycle trip, begun a long drive in a motor vehicle, or the like. In some cases it may not be completely clear that the routine/activity/task has begun until several minutes or hours afterward. Once the system or device has determined that such an a routine/activity/task has begun, the system or device can examine past data to establish the beginning or outset of the routine/activity/task and mark the beginning time. The system or device may also establish the beginning of the routine/activity/task through user input. The system or device can then also automatically determine the termination of the routine/activity/task, for example, by noting a cessation of detection of vigorous movement by a motion senor, or by noting in GPS coordinates an arrival back home or at some other known destination. Given the start point and the end point of the routine/activity/task, the system or device may then, through appropriate subtraction, compute or estimate the length in time of the routine/activity/task. Like the other values discussed in this application, this value may be stored, charted, reported, and/or used to provide notices or warnings to the subject.

Derived Measurements

A number of metrics may be computed, estimated, predicted, charted, and/or tracked in various embodiments of the present invention, based on measurements taken by the sensors of the present invention.

Heart Rate.

Heart rate (HR), also referred to as pulse, is commonly known to be the number of times a subject's heart beats in a time period, the typical time period being one minute. Heart rate can be measured directly from the subject by physically sensing the pulses attributed to the beats of the heart at numerous locations on the subject's body; the best locations, according to the American Heart Association, being the wrist, inside of the elbow, side of the neck, or top of the foot. However, such physical measurement of heart rate is not always viable, particularly while performing other activities. It is not only difficult to maintain pressure on the pulse point, count the beats, and maintain focus on the other activity or task, but it can be dangerous (e.g., a driver should not divert attention away from driving to check his or her heart rate, nor should a person exercising, such as on a treadmill, divert attention from the treadmill and proper running motion to do so). Fortunately, heart rate can be monitored in automated ways as well. Heart rate monitors (HRMs) measure and monitor a subject's heart rate, typically using either using a chest strap that places electrode sensors on the chest near the heart, or sensors of various types placed in other locations such as on the arm or wrist. Existing sensors have various shortcomings related to their placement on the body and type of sensor that can result in inaccuracy, especially during vigorous activity that has the effect of moving the sensor relative to the body. Many available systems tolerate the loss of sensor accuracy by providing estimations of heart rate when heart rate fails to become reliably measureable, using guesses involving assumptions about the maximum rate at which heart rate may speed up or slow down. While loss of accuracy and supplementation of lost data through estimation may be acceptable to the casual user, increased accuracy and reliability is a perennial goal in sensor development.

Alternatively, as in the present invention, a subject's heart rate can be measured far more accurately, precisely, continuously, and safely via other methods. Specifically, the present invention acquires a raw electrocardiogram signal from the subject which comprises the electrical biopotential signals output resulting from the functioning of the subject's heart. From this ECG signal, present invention extracts or derives a heart rate measure. This method is more accurate because it is taken directly from the ECG signal representing the heart's function, and does not rely on human intervention or requirements of simultaneous attention to counting beats and time while maintaining pressure on the pulse point. Further, this method is safer and more precise because the automated, computerized processing means allows for the user to maintain focus on whatever tasks or activities he or she is performing and does not require a splitting or sharing of attention between tasks and heart rate measurement—not to mention, again, the benefit of drawing the heart rate information directly from the ECG signal.

Deriving or extracting the heart rate from an ECG signal, however, does have some potential drawbacks. Often, physiological signals measured directly from a patient are subject to being corrupted by noise or artifacts from many different sources. Signal processing techniques, filtering, and other similar processes and methods allow for noise and artifacts to be removed, or for relevant, important portions of the signal to be extracted or otherwise differentiated from the noise and artifacts, and thus allow for accurate and precise measurement of the important and relevant portions of the signal. Several such methods are described at greater length herein, and are used with the present invention to ensure high quality, efficacious, accurate and precise signal and data processing and analysis to provide the most accurate data possible.

Heart Rate Variability.

Heart rate variability (HRV) is directly related to the subject's heart rate, and refers to the occurrence of differing time periods between heart beats. HRV is a measure of the variability of the beat-to-beat interval. HRV is thus effectively a measure of the reactivity of the heart to changes in metabolic need, and can be used to indicate dangerous conditions, usually as indicated by reduced or decreased HRV, that warrant attention by the user and possibly a medical professional. For example, decreased or reduced HRV is often associated with conditions or maladies including myocardial infarction, congestive heart failure, diabetic neuropathy, depression, sudden infant death syndrome (SIDS), and has been found to occur after certain procedures such as cardiac transplants. Additionally, HRV has been correlated to various psychological conditions, such as stress. HRV is related to emotional arousal. High-frequency (HF) heart rate variability activity has been found to decrease under conditions of acute time pressure and emotional strain and elevated state anxiety, presumably related to focused attention and motor inhibition. HRV has been shown to be reduced in individuals reporting a greater frequency and duration of daily worry. In individuals with post-traumatic stress disorder (PTSD), HRV and its HF component is reduced compared to normal while the low-frequency (LF) heart rate variability component is elevated. Furthermore, unlike normal, PTSD patients demonstrated no LF or HF reactivity to recalling a traumatic event. A theory in medical circles, called Polyvagal Theory, derives from a psychophysiologic imputation of importance to HRV. This theory emphasizes the role of HRV in understanding the magnitude and nature of vagal outflow to the heart. This theory decomposes HRV based on frequency domain characteristics with an emphasis on respiratory sinus arrhythmia and its transmission by a neural pathway that is distinct from other components of HRV, and is based on anatomic and physiological evidence for a polyvagal control of the heart. Thus, HRV plays an important role in both physiological and psychological human function, and monitoring or measuring HRV may provide valuable information and feedback to a subject and his or her medical providers.

Variation in the beat-to-beat interval is a physiological phenomenon. The sinoatrial node (SA node) receives several different inputs and the instantaneous heart rate or RR interval (referring to R as a point corresponding to the peak of the QRS complex of an ECG signal, and RR is the time period between two successive R points) and its variation are the results of these inputs. The main inputs are the sympathetic and the parasympathetic nervous system (PSNS) and humoral factors (those transported by the circulatory system), thus being closely related with the galvanic skin response sensors discussed herein. Respiration gives rise to waves in heart rate mediated primarily via the PSNS. Factors that affect the input are the baroreflex, thermoregulation, hormones, sleep-wake cycle, meals, physical activity, and stress. Decreased PSNS activity or increased SNS activity will result in reduced HRV. High frequency (HF) HRV activity (typically 0.15 to 0.40 Hz), especially, has been linked to PSNS activity. Activity in this range is associated with the respiratory sinus arrhythmia (RSA), a vagally mediated modulation of heart rate such that it increases during inspiration and decreases during expiration.

Accurate estimation or calculation of HRV is highly reliant upon accurate, continuous measurement of heart rate. If a single heart beat is not detected, and no smart algorithm is in place to interpolate the missing heart beat, the estimated or calculated HRV will be greatly affected by showing a very long interval between two successive beats as a result of the inappropriately or mistakenly missed beat. Even if a smart algorithm is in place to interpolate the missing heart beat, the missing heart beat may be interpolated in the wrong place and thus the HRV estimation or calculation may still be affected. Thus, it is imperative that the heart rate measurement must be precise, accurate and continuous. Methods involving determining heart rate from light reflectance or transmittance have not to date been found satisfactory, given that such readings may be spoiled by light leakage and motion artifact during vigorous movement. Thus, preferably, HRV is determined or estimated from heart rate data that is estimated or calculated from data sourced through ECG acquisition, preferably involving the removal or exclusion of artifacts and noise from the signal at its various successive levels.

There are many methods for determining heart rate variability, and they can commonly be broken down into two distinct groups: time-domain methods and frequency-domain methods, though other methods exist but are less commonly accepted. Time-domain methods focus on beat-to-beat intervals and analyze the time periods to obtain numerous variables that describe the variability. Frequency-domain methods apply a transform to the time-series ECG signal to convert it to the frequency domain and analyze the frequency domain signal to determine the number of intervals that apply to each frequency band. Common signal processing methods for frequency domain analysis can be used, including, but not limited to, power spectral density, fast Fourier transform (FFT), discrete Fourier transform (DFT), and the like. Time-frequency analysis methods, such as spectrogram methods, and non-FFT parametric methods, including the Lomb periodogram (for non-uniformly sampled signals like R-R timeseries), the Goertzel algorithm, and time-frequency analysis comprising parametric DFT methods, may also be used.

Respiration Rate.

Respiration rate is the frequency of ventilation, i.e., the number of breaths (inhalation-exhalation cycles) taken within a set amount of time. Respiration rate can be determined from ECG using a variety of techniques collectively called ECG-derived respiration (EDR). Two EDR techniques found by the inventors to be most effectively implemented using sensors attached to the head and/or arm are R-S modulation and respiratory sinus arrhythmia (RSA). The R-S modulation technique for determining respiration rate from ECG relies on the fact that the electrical dipole vector of the heart swings during inspiration and expiration. In ECG, the amplitude between the R and S peaks of the QRS complex changes based on the phase of this swing. By sampling and interpolating the R-S amplitude for every beat, then detecting the fundamental frequency of this envelope, respiration rate can be derived from ECG measurements. RSA, described above with repect to HRV determinations, is the speeding up and slowing down of the heart rate due to inspiration and expiration. In RSA methods of computing respiration rate, the R-R interval of the ECG signal is sampled to obtain an R-R time series (also called an R-R tachogram), and the fundamental frequency of the R-R tachogram is computed.

R-S modulation is computationally simpler, but RSA is more tolerant to noise and artifact. The target algorithm would use a combination of both, perhaps relying exclusively on R-S modulation when the signal is clean to maximize computational efficiency.

Stress.

Stress is generally defined as the response to a stressor or stimulus, and is an automatic response of the sympathetic and parasympathetic nervous systems reaction to the stressor or stimulus. Monitoring stress is effectively the process of monitoring a person's response to environmental stimuli. The goal of such monitoring is ultimately to, at a minimum, determine how a person reacts to a given stimuli, and preferably, to help him or her address the stimulus and reaction safely and effectively, and to help the person return to homeostasis, even in the continued presence of the stressor or stimulus.

Sleep Cycle.

Monitoring sleep cycle allows for the system or device of the present invention to determine the present state of consciousness of the subject, as well as to monitor and evaluate overall health, health practices and lifestyle of the user. Where sleep cycle data from many different users can be aggregated and analyzed together for various statistical features, such data can yield insights about the habits and health of populations and subpopulations and can evidence how various environmental or biological factors influence or interrupt such habits or impact the analyzed groups' health. Such environmental factors include seasonal changes in daylight, the workweek, the news cycle, cultural events like holidays and media sensations, natural or man-made disasters, prevalence and frequency of drug use including depressants such as alcohol and stimulants such as caffeine, etc. Likely the most significant biological factor in sleep cycle is the age of the subject, with older subjects having less sleep, but other biological factors may include gender, genetic factors, and disease state of the subject. Sleep cycle data can also be analyzed, either on an individual basis or for populations, to learn how sleep cycles correlate with or cause disorders. For example, it is believed that ADHD may result from interruptions in a regular bedtime schedule, and that clinical depression correlates with abnormal sleep patterns.

Sleep cycle can be derived or estimated from data from a variety of sensors or by combining data from such sensors. Data from body-mounted GPS sensors, for example, can provide a crude estimate of sleep cycle if assumptions are made that a subject who has not moved for a certain period of time, and appears to be in a safe dwelling place, is asleep. However, these assumptions fail when the person is stationary without sleeping (as when working at a desk or even while in bed) or when the subject is sleeping while in motion (as when sleeping on an airplane or train). Data from motion sensors can provide a better substitute or a supplement for such data, as stillness is consistent with sleep, but still cannot ascertain with certainty that a subject is asleep. Data from electroencephalogram (EEG) sensors provides a still better substitute or supplement for the aforementioned data sources, as sleeping subjects exhibit clearly different brainwave patterns. Video and/or audio may likewise be used as substitutes or supplements for the above. In some instances, even the absence of sensor data may be interpreted as indicating sleep if it is assumed that the subject only removes the body-mounted sensors of the present invention to sleep comfortably. It is contemplated that any sensor known in the art for the purpose of ascertaining sleep cycles may be used in the present invention so long as it is small and lightweight, consumes sufficiently low power, and may be worn and carried by the subject.

Alertness/Concentration/Focus.

Alertness is a measurement derived from signals of the various sensors that relates to the subject's level of focus, consciousness (similar to detecting sleep stage), awareness of the surroundings, and attention to a particular activity, task, object, or other such focal point. For example, an alertness metric allows the system or device of the present invention to determine whether the subject is daydreaming or otherwise losing focus on a particular task at hand, such as driving, reading, or working. Alertness can be derived from a single sensor measurement, such as an EEG, but in most instances is best determined by a combination and fusion of multiple sensor measurements, for example EEG in combination with eye tracking, though other combinations may work as well.

Preparedness (Stress+Alertness).

Preparedness is another metric that is derived from one or more sensors, and is essentially a combination of other, individual metrics the system or device may determine in various embodiments. For example, preparedness may be a combination of stress and alertness metric used to detect whether the subject is awake, focused and attentive to his or her surroundings or task, as well as the amount or level of stress the subject is experiencing. The preparedness metric may have particular utility for military applications such as for soldiers in the field, sports applications for players who may have suffered a potential concussion, first responders who can apply the system or device to injured parties, or the like. The preparedness metric would also provide utility for the casual user or work environments as well.

Calorimetry.

The number of calories burned during a particular exercise, activity, workout, or other period is a common metric used in various health tracking devices, heart rate monitors, lifestyle management devices, and the like. Calories burned may be estimated through knowledge of the type of physical activity engaged in, the duration of the activity, and personal information about the subject such as age, weight, height, gender, and the like. The information about the subject may be input by the subject while the knowledge of the type of physical activity engaged in and the duration of the activity may likewise be input or more preferably may be derived from GPS and/or motion sensor data (from accelerometers and/or gyroscopes), or from data transmitted from other devices such as treadmills or exercise machines. Motion and particularly the strength and frequency of detected body impacts may be analyzed statistically to classify time periods as running, jogging, walking, bicycling, rowing, performing calisthenics, resting, etc.

In some embodiments the present invention may be used to measure basal or resting metabolic rates or calories burned or metabolic rate during a particular activity or time period. With the user input and metrics measured or derived from the sensors of the system or device, the system or device can then calculate the various calorie or metabolic metrics and provide the information to the user. Preferably, the output is computed from known common formulas for calculating calories burned, which may be different for men and women. More preferably, the output is computed using statistical analyses and with the aid of a database of physical activity data generated from numerous subjects of varying ages, genders, heights, and weights. Many different methods or formulas are known in the art and can be used with the present invention.

Metabolism/Indirect Calorimetry.

A number of other metrics useful for gauging sports fitness or overall health may also be estimated, computed, predicted, charted, and/or tracked over time based on the sensor measurements taken and recorded by the present invention. Oxygen consumption ($VO_2$) or maximal oxygen consumption ($VO_2$ max) can be gauged in one of the various mask embodiments of the present invention with the use of an oxygen sensor, or may be more simply estimated, even without completely taxing the aerobic energy system of the subject, using one or more of a variety of estimations known in the art, such as the Uth-Sørensen-Overgaard-Pedersen estimation, the Cooper test, or the Leger-Lambert multistage fitness test. Other metrics that can be similarly estimated or computed and tracked/charted for the subject include carbon dioxide production ($VCO_2$), energy expenditure (EE) (i.e., heat production), respiratory quotient (RQ), and substrate utilization.

Advanced Recommendations.

The system or device of the present invention may further provide notices or warnings to the subject upon detection of various conditions relating to the measurements or estimated or predicted metrics. Such notices may serve as motivators or enticements, especially when based on predicted metrics, and/or may serve to "unlock" various personal "achievements" to assist the subject in meeting fitness goals. For example, the device or system of the present invention may deliver a notice to a jogging subject that if the jogger jogs one more mile at the present rate, the subject will set a new personal speed record for his or her jogging routine. The subject, receiving the notice, may then be motivated to maintain or increase pace in order to set the new record. As another example, the device or system of the present invention may deliver a notice to an exercising subject when a recent meal has been "worked off" through exercise by gauging the number of calories of energy expended during an exercise activity or routine and comparing this number to the number of calories consumed in the meal. The number of calories consumed in the meal can either be pre-input by the subject through a user interface, or determined by automated methods. As one example of an automated method of determining the caloric content of a meal, the user may scan a barcode or QR code found on the packaging of the meal, or other identifying packaging or descriptive labeling, with a smartphone camera or similar scanning device linked with or incorporated into the device or system of the present invention, and the caloric content of the meal is then retrieved from a database for comparison. In a similar example, the user could be notified when a sufficient number of calories have been expended (or are about to be expended) to justify consumption of a reward meal or snack, where the reward meal or snack may be one known to be a favorite of the subject (either from input preferences or from information harvested from social media) or one provided as a promotional advertisement from a sponsor manufacturer or restaurant. An enticement may include the activation or unlocking of a coupon for a food product or other item or service. Other advanced recommendations may include, without limitation, notifications of when it is time to begin or cease an activity, when it is time to rest or go to sleep, when it is time to wake up, when bodily fatigue is imminent, when activity or relaxation should be engaged in to prevent or forestall a hazard condition (such as a pressure ulcer, joint irritation, or the like), and similar. The advanced recommendations may appear as text on a display, as verbal announcements supplied through soundspeakers, as any combination of text, graphics or motion images supplied on a video display, or in any other fashion. These are but a few examples of advanced recommendations that may be provided to a subject making use of the device or system of the present invention.

The device or system of various embodiments of the present invention may also devise and propose tests or experiments for the subject to undertake which may make use of the scientific method to eliminate variables and thereby settle on the true causes of certain conditions, or, alternatively, may analyze already-collected data to carry out largely the same scientific function without the need for alerting the subject that the test is to be conducted. For example, if the subject reports to the device or system an undesired feeling or sensation, and the device or system is provided with information about the diet of the subject and has also collected exercise activity data, the device or system can test the effects of the known various dietary choices and exercise activities with the feeling or sensation by testing for statistical correlations between the various dietary/exercise inputs and the feeling/sensation results as reported at various times over a period. A database of test regimens may be supplied to the device or system through, for example, the Internet, and may be customized by the device/system for the individual subject, allowing the device/system to tell the subject to engage or refrain from certain dietary choices or exercise activities during certain periods so as to complete the needed data collection and promote the analysis. Thus, for example, the device/system can test the effects of subject choices on the subject's metabolism, and then recommend those activities or comestibles that increase or decrease metabolism as desired by the subject.

An advanced assisted heart rate training program is another example of a function that may be provided by the device or system of the present invention in various embodiments. Although heart rate training can be done with simpler heart-rate monitors, doing so requires significant understanding, thought, and computation on the part of the individual trainee. The present invention simplifies the training by supplying simple instructions and suggestions and providing easy-to-understand quantitative summaries of collected data. In heart rate training, by making use of measurements during activity and while at rest, the device or system of the present invention can assist the subject in fine-tuning physical activity, especially high-intensity activity such as running, by making suggestions and giving instructions that lead the subject to engage in the optimal intensity of the activity.

Heart rate training involves, at the outset, the device or system estimating or determining the subject's heart rate response to various activity intensities. Three heart rates are of special interest: the resting heart rate, the lactate threshold heart rate, and the maximum heart rate.

The device or system estimates the subject's resting heart rate by measuring the subject's heart rate at an appropriate time, such as when the subject wakes up prior to getting out of bed, or more preferably by computing a rolling average of such measurements collected over a time period, such as the last week or the last month, with outliers omitted from the computation. This can be determined automatically and no special instructions are needed to be provided to the subject, so long as the subject can comfortably wear the sensors of the present invention to sleep, or is instructed to don the sensors immediately upon waking up without exerting substantial physical effort.

The device or system determines the subject's lactate threshold heart rate while the subject is exercising at an intensity at which lactic acid accumulates in the blood stream, an intensity level generally corresponding to the highest intensity of activity that can be sustained without the subject experiencing significant discomfort and a large increase in breath rate. The device or system provides the appropriate instructions, encouragements and enticements necessary to impel the subject to perform such activity. For example, the system may instruct the subject to jog at a comfortable pace for two or three minutes, then to increase and sustain pace slightly for another two or three minutes. When the system notes a spike in breathing, either through sensors capable of detecting breath rate, or through user input of such a spike, or most preferably through ECG methods of detecting respiratory rate as described above, the detected heart rate at the previous level of activity intensity is deemed the lactate threshold heart rate.

The device or system estimates the subject's maximum heart rate by selecting the maximum heart rate detected from the subject during a particular activity designed to elicit all-out physical effort. Examples of such activities include running a competitive 5-kilometer race, or 2-mile time trial at maximum sustainable effort on a track or a roughly flat stretch of road. As before, the device or system provides the appropriate instructions, encouragements and enticements necessary to impel the subject to perform the particular activity. Alternatively, the device or system can estimate maximum heart rate using a formula that takes into account subject-input factors such as age and fitness level. One simple formula subtracts the subject's age from 220 to arrive at an estimated maximum heart rate.

The device or system can compute the subject's heart rate reserve by subjecting the subject's resting heart rate from the subject's maximum heart rate.

With these values established, the device or system of the present invention devises work-out routines and work-out schedules based on pre-defined templates, the subject's preferences, measured or estimated data collected from the subject during workouts, and/or statistical data collected from or representative of other trainees, and preferably other trainees similar to the subject in age, fitness level, and other factors. The individual work-out routines induce the subject to exercise for a time period less than a day within a variety of target heart rate "zones," while the work-out schedules alternate more challenging with less challenging work-out routines over a time period of weeks, months, or years to encourage regular physical activity and promote overall lower subject heart rates, both maximum and resting, indicative of healthy and sustainable cardiovascular development. The work-out routines and schedules are presented to the subject through the aforementioned instructions, encouragements and enticements, as well as, optionally, through modification of the subject's personal calendar to include work-outs scheduled at convenient times, as permitted by the subjected. The device or system can advise the subject when "It's time for your daily workout," for example, and can suggest automatic rescheduling of the workout if it appears from sensor measurements that the subject is not performing the workout.

Examples of various zones can be warm-up or recovery zones at 60 to 70 percent of heart rate reserve plus resting heart rate; aerobic zones at 70 to 80 percent of heart rate reserve plus resting heart rate; anaerobic zones at 80 to 90 percent of heart rate reserve plus resting heart rate; and extreme or "red line" zones at 90 to 100 percent of heart rate reserve plus resting heart rate, the last of which involves lactic acid buildup and thus should be programmed for only short periods within a work-out routine. When it is time within a work-out routine for a transition to a more or less challenging zone, the device or system provides an instruction or notification to the subject to "pick up the pace" or "slow down," for example; determines the subject's heart rate and/or other parameters of interest, and issues a follow-up instruction or affirmation to induce the subject to adjust or maintain activity intensity so as to transition to or stay within a target zone according to the pre-defined work-out routine.

An example of a simple work-out routine template is as follows: 10 minutes of warm-up activity, targeting a first heart-rate zone; followed by 10 minutes of more intense activity targeting a second heart-rate zone; followed by 5 minutes of maximum intensity activity, targeting a "red line" zone; followed by 10 minutes of cool-down activity, targeting the first zone again Innumerable such templates can be devised and revised using known methods, and can be refined to meet the subject's fitness goals and workout preferences as the subject's physical fitness apparently improves with reference to fitness statistics collected from comparable populations and provided to the system or device through, e.g., the Internet.

In similar fashion, with or without the above-described training, the device or system of the present invention can provide testing to determine subject preparedness for a goal activity or mission. Preparedness in this context is defined as the apparent physical ability, including speed, endurance, stamina, etc., to complete a physical task, such as finishing a marathon or triathlon, completing a hike or mountain climb, participating in a strenuous military mission or training exercise, staying awake and alert for a long drive, or the like, as determined by testing the subject either under activity-simulating conditions or under conditions which are known to correlatively demonstrate preparedness. In such a way, the device or system can advise the subject or the subject's superior or regulator that the subject is or is not prepared to run the marathon, complete the hike, fly the mission as a pilot, etc. based on quantitatively collected data and known activity requirements. For example, if the device or system is supplied with the known resting heart rates and maximum heart rates of race qualifiers, the device or system can evaluate the subject as prepared or unprepared for the race based on its measurements or estimates of the same parameters for the subject, and then further optionally suggest a training regimen, as described above, to maintain, improve, or achieve the subject's preparedness.

Actuators

Haptics.

Haptic technology provides tactile feedback that stimulates the sense of touch by applying forces, vibrations, or motions. Haptic actuators include vibrators, as are common in cell phones and video game controllers, and actuators that suppress motion, as by locking joints or pressing against limbs. A simple vibrator is made with an eccentric rotating mass (ERM), which involves a mass spun by a motor on an axis off its center of mass. Different effects (and thus different distinguishable signals to the user) can be created by pulsing the spins with different durations, pulse frequencies, and/or duty cycles, and/or by altering the spin speed. More advanced vibrators use linear resonant actuators (LRAs), which vibrate a magnet attached to a spring and surrounded by a coil when current is applied, or piezo beams or disks, which deform on the application of current. Different effects (and distinguishable signals) can be achieved with these actuators as with ERMs. The present invention further envisions haptic actuators that function by pressing or vibrating against pressure points, for example, by pressing against or massaging one or more temples of the head to automatedly relieve maladies such as migraine headaches, nausea, and seasickness upon detection of such a malady or upon being informed of such a malady. These haptic actuators may be incorporated in the eyewear or other headgear of the present invention.

Shock.

Electrical stimulators use electrodes to deliver mild electrical currents to parts of the body. Stimulation is typically applied as a series of pulses. Insufficient current density will have no appreciable effect as it will not innervate the target neurons to bring about the desired signal to the subject, but too much current density, or current density applied over too long a period of time, can cause hyperthermia to tissues, damaging them. Electrical stimulation pulses should be applied in a safe manner so as not to damage tissue. The safety of the electrical stimulation depends on a number of factors, including the duration and number of pulses and the size of the electrodes with which they are applied, as well as tissue impedance and the ability of tissues to quickly transmit away heat energy. Where the electrodes are small and act as point sources of current, the damage threshold is determined by the total current, whereas with larger-diameter electrodes, the damage threshold is determined by current density, which scales with pulse duration as the reciprocal square root of time of pulse. Methods and computations known in the art for supplying safe, effective electrical stimulation should be employed and caution should be exercised when using stimulation. In the embodiments of the present invention, the risk of life-threatening stimulation is lessened through use of small battery power for any stimulator and by the absence of stimulator current paths through the heart.

Light Actuators.

Certain other actuators permit for gradual or more rapid changes in the environment of the subject, including ambient light. In the cases of eyewear and masks, for example, small lights such LEDs or other light emitters may be placed in proximity to the eyes and may glow, flash, or blink. Preferably, this placement is along the diameter of lenses on the inside of the eyewear frames. Alternatively, larger light emitters (LEDs or otherwise) placed elsewhere and adapted to be in communication with the present invention may be used to provide notices or warnings by illuminating, de-illuminating, flashing, etc. Alternatively, visors, lenses, and goggles may be made with any technology known in the art to be capable of electronically tinting glass or plastic lenses or visors, and thus to permit outside light to slowly (or quickly) enter from an initial darkened state. One such technology is the AlphaMicron E-TINT technology, which use a mixture of dichroic dyes in a liquid crystal host sandwiched between flexible plastic substrates coated with transparent electrodes. With this technology, transmissivity and color are changed when voltage is applied to the substrates and an electro-optic response is induced in the liquid crystal; the tint can be fully activated in about half a second. In embodiments of the present invention involving eyewear, such lights or tinting actuators can gradually increase light stimulus delivered to the subject over time, as with a graduated alarm clock, or may provide more rapid light changes to alert the subject to an alarm condition or to rouse the subject from a drowsy state.

Soundspeaker.

A soundspeaker can provide sound signals, including music or speech, to the subject, for example, as implemented in earphones used in headphones or earbuds, or as implemented in some other device placed near the subject, such as a smartphone, car stereo, alarm clock, or entertainment system. If a soundspeaker is not implemented directly in the device of the present invention, the device can communicate the sounds to be produced, or transmit instructions to produce sounds, to a nearby device on a wired or wireless connection, including Bluetooth, WiFi, or any other protocol known in the art. As described above with respect to light actuators, it may be desirable in certain circumstances, to produce a sound signal of gradually increasing intensity in order to more gently alert or arouse the subject.

Computer Interface/Video Screen/UI.

Many embodiments of the present invention include a visual display or other visually-stimulating system. Various types of devices are known in the art for generating a visual signal, even in miniature systems that are worn on the head or the eye. In some embodiments, the display may consist of a video monitor, set apart from the device of the present invention, which the device may send (and in some cases receive) signals to (and from). In other embodiments, the display may be similarly separated from the device of the present invention but may be integrated into an interfacing device such as a digital music player, PDA, smartphone, watch, health monitor device, or the like. In other embodiments, particularly those involving eyewear, the display is integrated into the device of the present invention, in which case it is preferably small enough to be worn comfortably on the body, and preferably as a head-mounted display (HMD), as with the displays now in use on smart eyewear devices such as GOOGLE GLASS and similar devices. Such embodiments may employ one or more of a number of different display technologies, including a heads-up display (HUD) accomplished through (1) a liquid crystal display implemented in an eyewear lens; (2) projection onto a transparent prism situated in the subject's field of vision; (3) an optical waveguide (diffractive, holographic, polarized, reflective, etc.); and/or (4) a virtual retinal display (VRD), also known as a retinal scan display (RSD) or retinal projector (RP), which draws a raster display onto the retina of the eye using one or more beams of coherent light. In any instance, the display permits the perception of a "hovering display" of generated images overlain on the subject's vision of the real world. In such implementations, the resolution of the display is preferably at least 640 by 360 pixels.

Temperature Actuators.

Some embodiments of the present invention may also communicate to a temperature control device, such as a heater, air conditioner, or miniature thermal actuator, to provide a temperature change or temperature signal to the subject. For example, if an unwanted drowsiness condition is detected in the subject, an appropriate embodiment of the present invention may send a signal to a vehicle climate control system to adjust the temperature (e.g., to switch on the air conditioning) in order to ameliorate a drowsiness-inducing temperature, or may activate a miniature temperature actuator incorporated in the device or placed nearby on the body of the subject to send a cooling or warming feeling that is effective to rouse the subject or to alleviate discomfort or pain that the device has either detected or been alerted to.

Ear Pressure Equalization.

In some embodiments of the present invention, and particularly those which use earbuds or similar devices which may close off the ear canal to the outside world, preferably such devices include an actuator to opens a passage to equalize the pressure between the ear canal and the ambient environment. The actuation is felt by the subject as a puff of air to "pop" subject's ear. Such an improvement is important where the subject may be gaining or losing altitude, as in aerospace applications, standard air travel, mountain climbing, and for persons who work on tall buildings or in deep mine shafts and may travel on elevators. Such an improvement prevents the subject from needing to remove the earbuds or similar devices in order to achieve the relief of air pressure equalization in the ear(s).

Power and Energy Harvesting

The device embodiments of the present invention are preferably small, lightweight, and totally portable, meaning they can be comfortably worn on the body and carried with ease. Power is provided to such embodiments by a small battery. Preferably, the battery is replaceable and/or rechargeable. The battery technology may be selected from any suitable type known in the art, including replaceable alkaline or replaceable rechargeable such as nickel-cadmium or nickel-metal hydride, lithium-ion, lithium polymer, etc. Especially in embodiments that include a wired data transfer port such as a USB connection, the battery may be advantageously recharged using the same cable as the one used for data transfer and during the same time as data transfer, using power connections in the transfer cable. Inductive methods of power transfer known in the art and implemented in a number of sealed rechargeable devices may also be advantageously employed for recharging the device embodiments of the present invention.

More preferably, the device of the present invention is capable of supplementing its energy supply by harvesting energy from the subject or the environment. Photovoltaic, piezoelectric, and biomechanical-kinetic methods for energy harvesting are known in the art and may be advantageously employed in the present invention. For example, a ballcap embodiment of the present invention may collect solar energy using a flexible photovoltaic surface applied to the cap and brim to supplement its battery charge, while a wristwatch or eyewear embodiment might utilize the kinetic energy of the body or a limb during movement to wind a mainspring or to move a magnet in an electromagnetic generator to produce supplementary energy.

DESCRIPTION OF THE PREFERRED EMBODIMENTS

FIGS. 1A, 1B and 1C illustrate an earbud embodiment of the present invention, in which sensors 12, 16 are mounted along the outside rim 13 of the earbuds 11. As illustrated, dry electrodes 12 incorporating surface features such as bumps or penetrators are used to acquire ECG or other electrophysiological signals. The surface features improve the quality of the acquired signals and/or assist to keep the earbud secure in the ear, thereby also improving acquisition during vigorous activity by reducing motion artifact and loss of sensor contact with the skin that can result from jostling. Other sensors 16 may be infrared or of any other suitable type listed above in this application. The earbud 11 further incorporates a soundspeaker 18 through which music, speech, instructions, notifications, warnings, or reports may be delivered. In some embodiments the tempo of the delivered music may be adjusted to the pace of the subject's physical activity, e.g., delivered music may be sped up as a jogger runs faster, as detected by motion sensor data, GPS data, heart rate measurements or estimates, or measurements from or estimates based on any other suitable sensor or suite of sensors.

Use of two electrodes permits the ECG to be measured based on two points on different sides of the head. A third electrode can provide a ground or reference. The third electrode can be implemented in the earbuds (as illustrated) or in some embodiments may be placed elsewhere on the body, like on the torso or arm, and in such case may be integrated into a separate device such as a music player, smart phone, watch, etc.

Preferably, rim 13 is made of an electrically insulative material so as to keep the electrophysiological sensors 12 electrically isolated from one another. The rim may be made of a non-toxic silicone polymer or a harder plastic. Preferably the rim fits in the ear so as to provide a good seal and to keep the earbud anchored.

The earbuds may receive audio from a separate device (24, 25, 26 in FIG. 2) or may have a built-in digital memory (not shown), preferably a non-volatile flash memory, for digital storage of media files.

Figure 2:
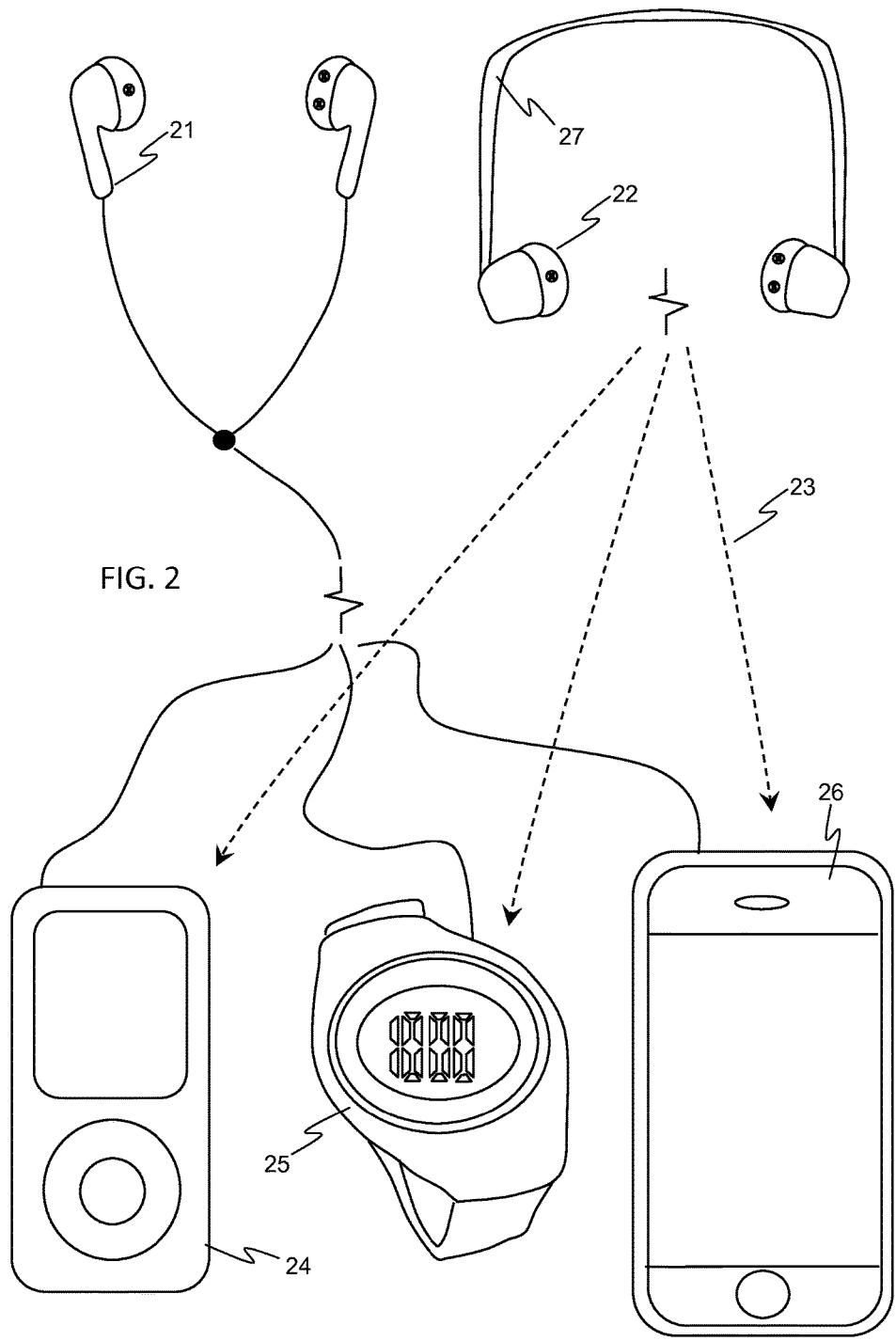
FIG. 2. Communication between the earbud embodiment and other device(s).

Optionally, the earbuds may be connected to each other and/or to an input and/or output device (such as a digital music player, smart phone, or health data monitor) by wire 14. In some embodiments, preferably, wire 14 is a mere tether to keep the earbuds together physically. In such embodiments, or in other embodiments in which there is no wire 14, the earbuds preferably communicate with each other and/or with another device using a wireless protocol such as Bluetooth or WiFi to transmit digital audio and acquired sensor measurements. In other embodiments the earbuds may be tethered together (with wired signal connection or not) by a more rigid connector 27 that fits around the head and helps to keep the earbuds snugly in place (as shown in FIG. 2).

Preferably, the earbuds also have one or more of the other above-listed sensors incorporated into the housing 11, such as MEMS motion sensors (accelerometer/gyroscope) (not shown).

Data collected by sensors may be recorded to a non-volatile flash memory or other memory incorporated into the earbuds (not shown) or to one or more of the connected devices 24, 25, 26, and may be retransmitted wireless or transferred through a wired feed, such as by USB, at a later time, for storage or analysis on another computer or device (not shown). Preferably, the battery of the earbud may also be recharged either through a USB connection or through an inductive power transfer.

In alternate embodiments, headphones with integrated sensors are used instead of earbuds, with the dry electrodes and/or other sensors placed on the rims and/or insides of fitting headphone earcups so as to press against the skin and provide good electrical contact and lower motion artifact.

Figure 3:
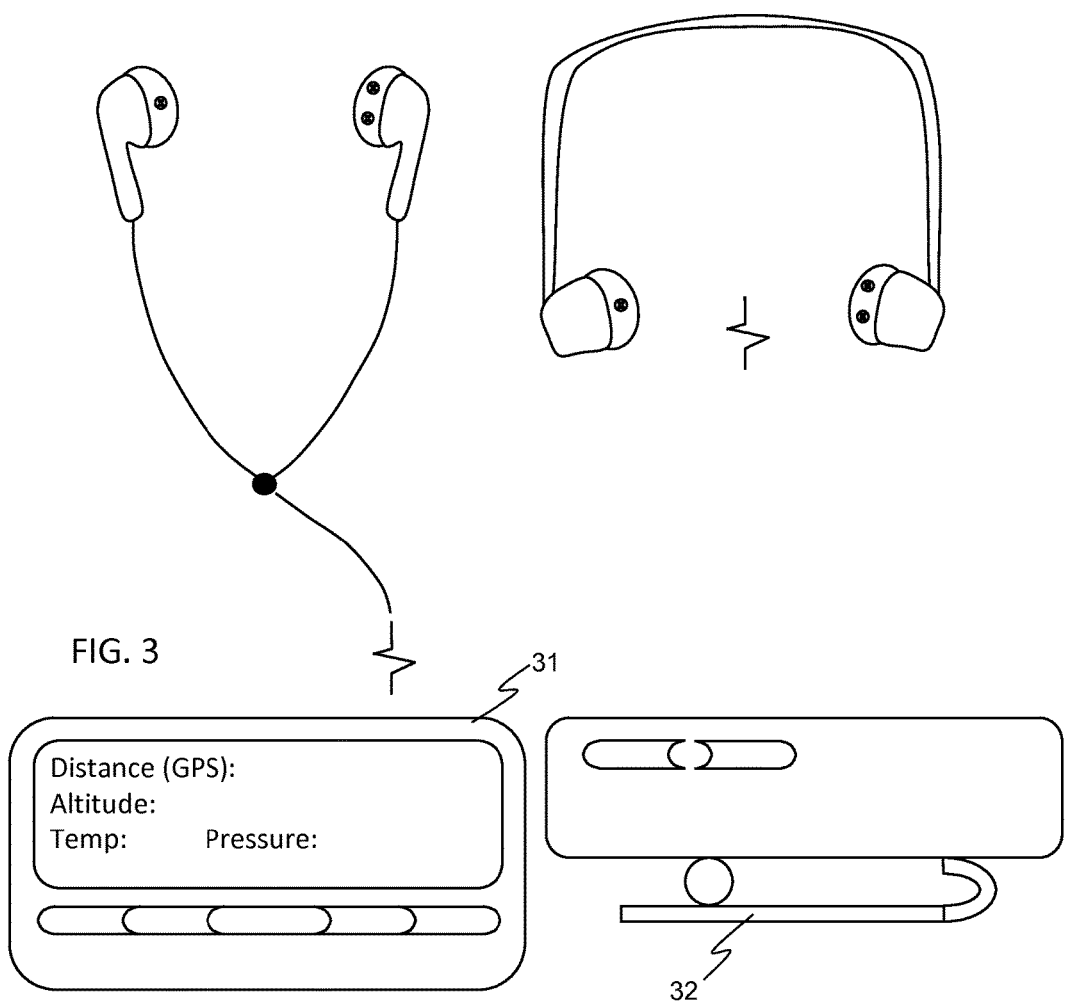
FIG. 3. Communication between the earbud embodiment and a health monitor.

As shown in FIG. 2, the different styles of earbuds 21, 22 may either be wired (21) or communicate wirelessly 23 (22) with one or more other devices worn on or placed near the subject's body during the fitness routine/activity or occupational task. These may include a digital music player 24, watch or smart watch 25, smart phone 26, or other electronic device such as a PDA, health monitor 31, etc. As shown in FIG. 3, health monitor 31 may be a small electronic device with a display screen showing measured, computed, estimated, derived, or predicted metrics and preferably also including a user interface to scroll through and/or customize the metrics displayed. Preferably, a clip 32 is provided to clip the health monitor to the clothing of the subject, or an armband, chest band, or headband. As mentioned previously, the health monitor may further include additional sensor(s) of the types already discussed. A dry electrode incorporated in the monitor 31 or its clip 32 may serve as a ground or common electrode.

FIG. 4 shows another embodiment of the present invention consisting of sensors implemented in wireless earbuds 42 useful for detecting whether the subject is drowsy or alert, focused or unfocused during an occupational task such as driving a vehicle or operating dangerous machinery such as heavy construction equipment or factory equipment. Such sensors preferably comprise ECG, EEG, motion, and/or temperature sensors, as well as ambient and/or ear bone microphone(s). During normal operation the earbuds may deliver music and/or keep the subject in one- or two-way radio communication with a home base. Optionally, sensed, computed, estimated, or predicted statistics or metrics may be displayed 40 for the subject or may be transmitted back to a home base, providing safety-related feedback to supervisors. Upon detection of a condition such as a reduced heart rate, a change in brainwave pattern (particularly a transition from beta to alpha, theta, or delta waves) or a combination of conditions such as lack of substantial motion over a predefined threshold period of time in combination with temperature above or below a threshold (indicating possibly sleepiness), a notification or warning 41 may be delivered to the subject, either through a visual display (in a moving vehicle, preferably this is a heads-up display incorporated into the dashboard and/or windshield) that is in communication with the earbuds through a wireless connection, and/or through an alarm or speech message delivered through the earbuds or other audio device. The present invention may further trigger the driven vehicle to initiate automatic braking, automatic steering, or other autopilot features, or may trigger any other equipment to shut down and/or put itself in a less dangerous state, either contemporaneously with the notification/warning to the subject, or within some predefined period of time thereafter, or if the system/device determines that the notification/warning has been ineffective in focusing or rousing the subject by sensing the persistence of the drowsy or unfocused state and/or the lack of appropriate response to the notification/warning. As discussed earlier, the notification or warning may be delivered as a visual or audible stimulus or as a temperature change using a temperature actuator or as a mild electrical signal using a stimulating electrode, or as any other suitable type of stimulus such as those discussed previously in this application. Although FIG. 4 shows earbuds 42, it is envisioned that any of the headgear or eyewear embodiments may be implemented to similar effect in a drowsy-driver, impaired-driver, or distracted-driver warning system.

Figure 5A:
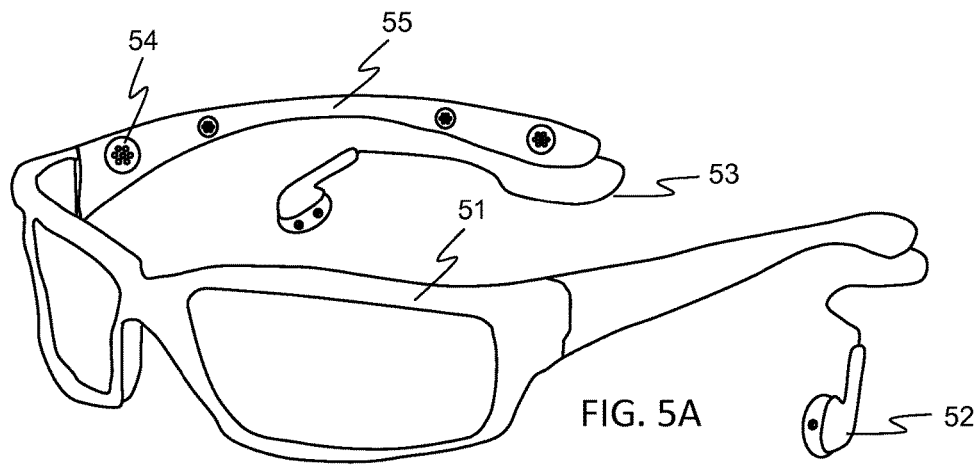
FIGS. 5A-5G. Eyewear apparatus embodiment(s) of the present invention.
Figure 5B:
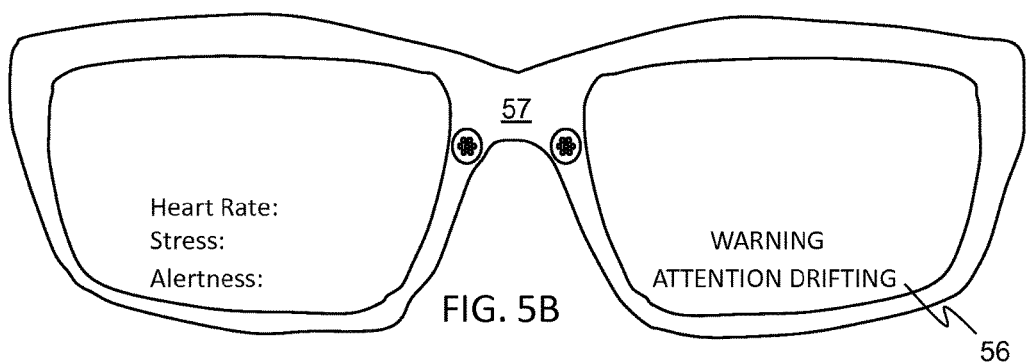
Figure 5C:
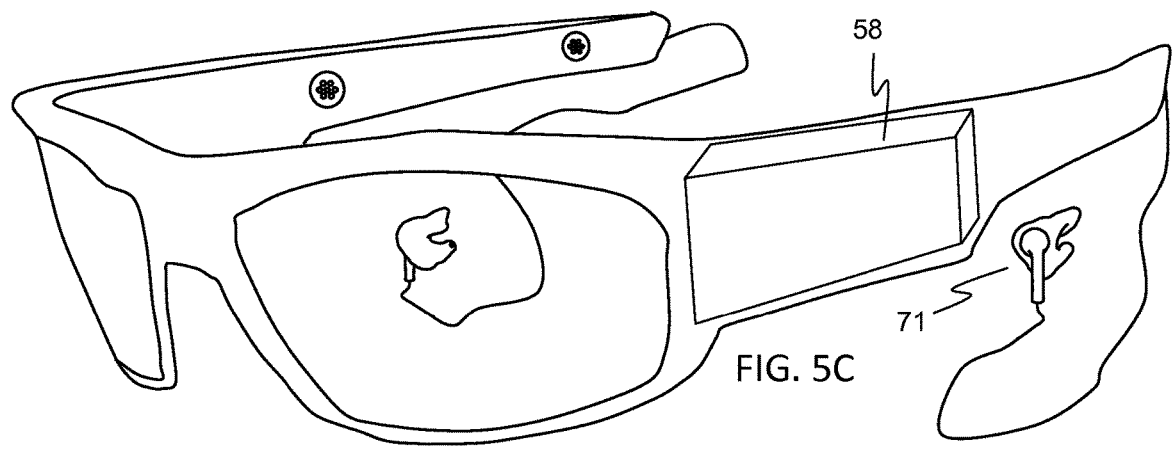
Figure 5D:
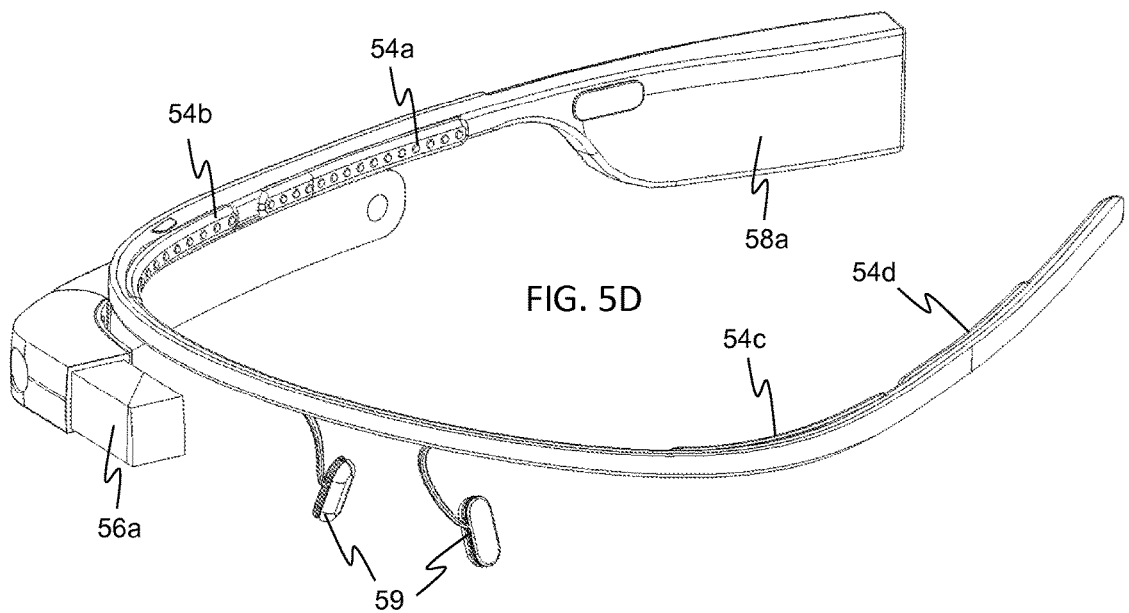
Figure 5E:
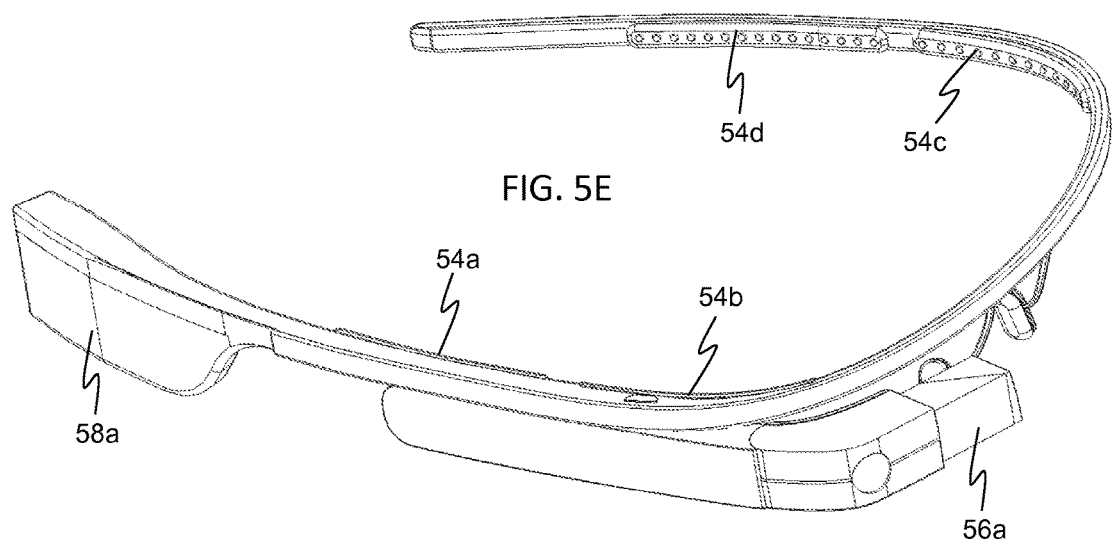
Figure 5F:
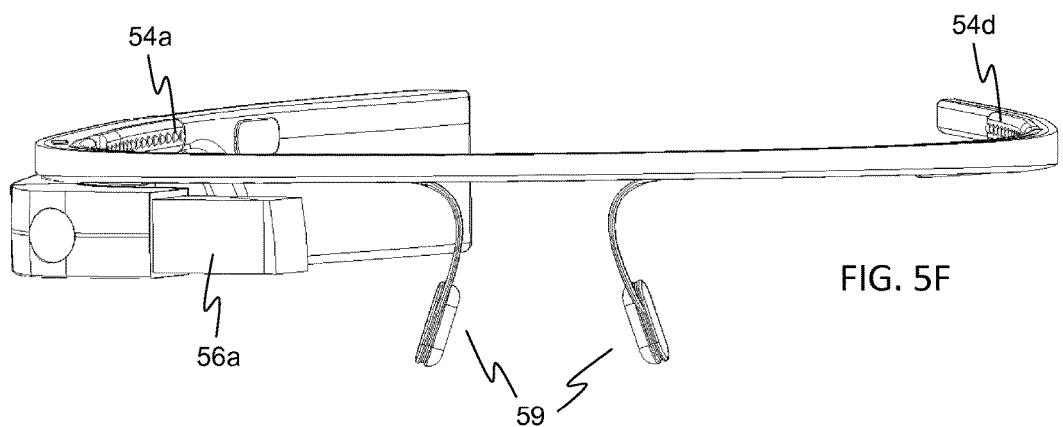
Figure 5G:
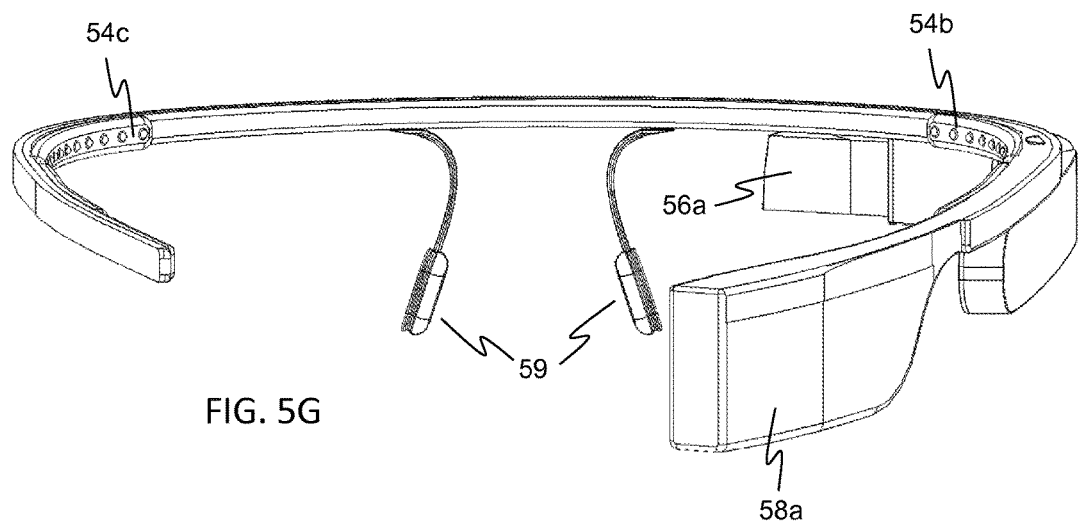

Rather than using earbuds for the same or similar application, eyewear as shown in FIGS. 5A-5C or 5D-5G may be used. The eyewear 51 as illustrated in FIGS. 5A-5C incorporates earbuds 52 attached to the eyewear by wires 53, but the earbuds may be wireless and interface with the eyewear or another device by means of a wireless protocol, or the earbuds may be omitted entirely and the device may be limited to the eyewear only (not illustrated). Sensors, and in some embodiments preferably dry electrophysiological sensors 54 having surface features, may be integrated into the temple stems 55, the nose bridge 57, or nose pads (not shown) to detect electrophysiological signals from the head of the subject. These and other sensors may be implemented at any appropriate place on the eyewear frames, but particularly in the case of electrophysiological sensors, the sensors are advantageously placed at points where the frames provide natural pressure against the skin of the subject—especially along the temple stems and nose bridge. Measured values, calculated/estimated/predicted statistics, notices or warnings 56 may be delivered to the subject in the subject's field of vision using any of the HMD technologies discussed above or by any other method known in the art. Depending on the particular embodiment, lenses may be present or omitted depending on the display technology used or omission thereof. If earbuds 52 are incorporated, or if another audio device is present nearby, audio notifications or warnings may be delivered as well. Other sensors may also be integrated into the glasses, such as MEMS motion sensors, to provide any of the aforementioned data acquisition or to drive a user interface controlled through head gestures/postures/motions such as nods, tilts, or shakes. If necessary additional frame housing 58 may be provided to house sensor(s), processor(s), actuator(s), and associated electronics (for amplification, processing, and transmission of collected signals, for the subject's interfacing with the eyewear device, for display or feedback, or for wired or wireless transmission or storage of data on the frames of the eyewear. Preferably the weight of these components is distributed symmetrically on the eyewear. Preferably, the electronics, sensors, and other components are integrated into the eyewear frames as closely as possible and with the edges being smoothed so as to avoid an ungainly boxy appearance and provide a more natural style. In some embodiments, preferably, dry electrophysiological sensors forward on the temple stems and nearer to the eyes are used to collect EOG signals while dry electrophysiological sensors back on the temple stems over the ears are used to collect ECG signals. The inventors have found that this arrangement is particularly well adapted to collecting EOG and ECG signals from the head. EOG signals can be used to detect eye movements and blinks which in turn can be used to drive the user interface of the system or device. For example, a detected double-blink, or blinks or certain duration or intensity, can be programmed to perform certain UI navigational tasks, such as substitutes for mouse clicks or finger points in more traditional user interfaces, while estimated or derived eye direction or orientation can be used as a substitute for a pointer in more traditional user interfaces.

In embodiments illustrated in FIGS. 5A-C, the dry electrophysiological sensors are round and have radially-symmetrical arrangements of surface features, but in some embodiments, preferably, the electrodes are shaped to be elongated and to have linear arrangements of surface features, e.g., one or two rows of bumps or penetrators extending along the temple stems. Such an arrangement permits for temple stems to be naturally thin while still providing sufficient room and surface area for the dry electrophysiological sensors. In any case, the shape and fit of the eyewear naturally provides sufficient pressure to press the dry electrophysiological sensors against the skin of the subject to maintain good electrical contact, particularly in conjunction with the action of the surface features, which assist in holding the electrodes in place against the skin, even during vigorous activity, ensuring a minimum of motion artifact. The disclosed arrangements are capable of producing clean ECG solely from the head even when the subject is moving his or her head vigorously.

Another eyewear embodiment is shown in four different views in FIGS. 5D-5G. This embodiment has four dry electrodes 54a, 54b, 54c, 54d, each with a linear arrangement of bumps or penetrators which variously make contact with the skin above the ears (54a, 54d) or at the temples nearer the eyes (54b, 54c) on both the left (54c, 54d) and right (54a, 54b) sides. This configuration provides good contact and signal collection even through the hair of the wearer. Additional sensors, including other dry electrodes, temperature sensors, galvanic skin response sensors, NIR sensors, and/or pulse oximetry sensors may be implemented in the nose pads 59 and thereby make good contact with the skin. A head-mounted display (HMD) 56a provides visual information, including instructions, to the wearer. Additional frame housing 58a may be provided to house sensor(s), processor(s), actuator(s), and associated electronics (for amplification, processing, and transmission of collected signals, for the subject's interfacing with the eyewear device, for display or feedback, or for wired or wireless transmission or storage of data on the frames of the eyewear. Preferably, the weight of the eyewear is balanced symmetrically across the wearer's head for comfort. There may or may not be lenses (not shown).

Other in-the-ear embodiments of the present invention are shown in FIG. 6 and FIGS. 7A-7B. Operating similarly to the earbud embodiments previously described, the wired or wireless in-ear hearing aid 61 of FIG. 6 advantageously incorporates one or more sensors as described above, preferably including dry electrode(s) preferably having surface features. The hearing aid 61 may fit to the concha of the ear and/or may also partially fit into the outer ear canal of the subject to provide additional fit and security from motion artifacts and/or to place sensors (e.g., for measuring temperature) further in the ear canal and closer to the eardrum. Wireless or wired earbuds 71, as shown in FIGS. 7A-7B, may also be custom-molded to perfectly fit the ear of the subject, including concha and/or outer ear canal, using any custom-molding fabrication method known in the art, including by taking casts of the subject's ear(s) and/or by laser scanning measurement and/or other photogrammetric measurement. A custom-molded earbud has the advantage of providing an even closer, tighter fit that is capable of withstanding even more rigorous physical activity and jostling, and thus providing even higher-quality signals.

Figure 8:
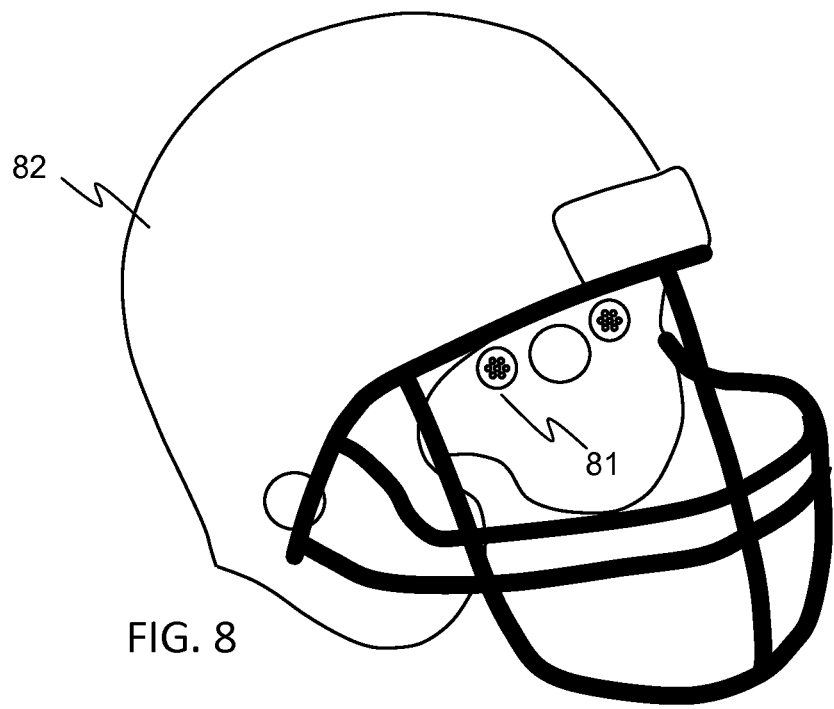
FIG. 8. A sports helmet embodiment of the present invention.
Figure 9:
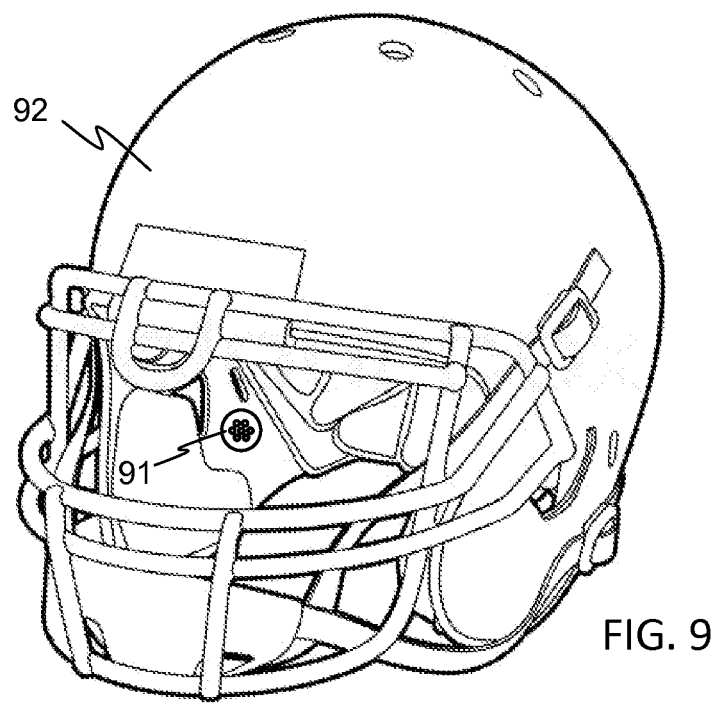
FIG. 9. A sports helmet embodiment of the present invention.

FIGS. 8 and 9 show helmet embodiments of the present invention, with the dry electrophysiological sensors 81, 91 (preferably having surface features as described previously) and other sensors, actuators, and features of the present invention incorporated into sports helmet 82, 92. Interior padding provides a tight, comfortable fit and the necessary pressure to keep the dry electrodes 81, 91 pressed against the skin so as to make good electrical contact and to reduce or eliminate motion artifacts.

Figure 10:
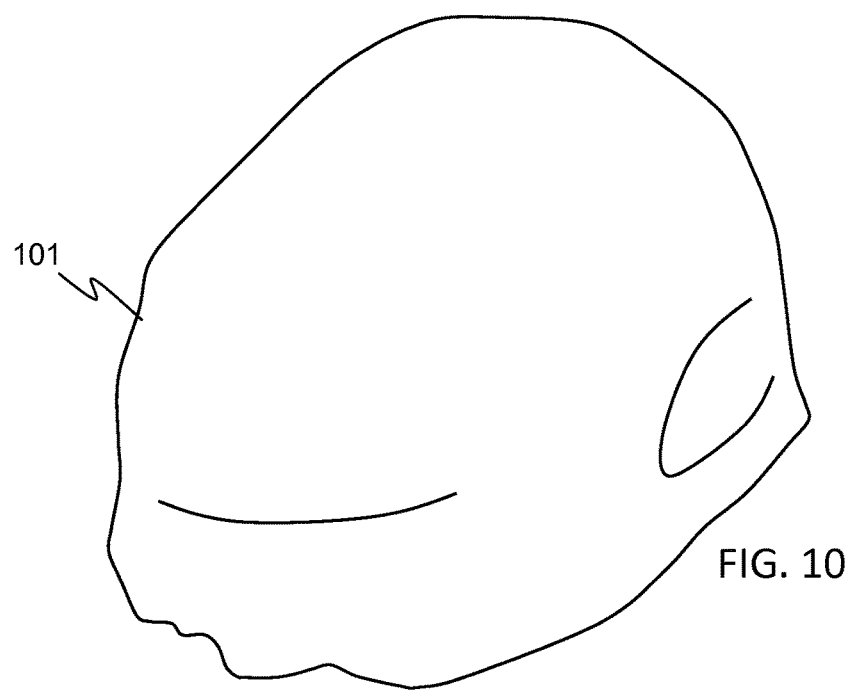
FIG. 10. A swim cap or similar tight-fitting skull cap embodiment of the present invention.
Figure 11:
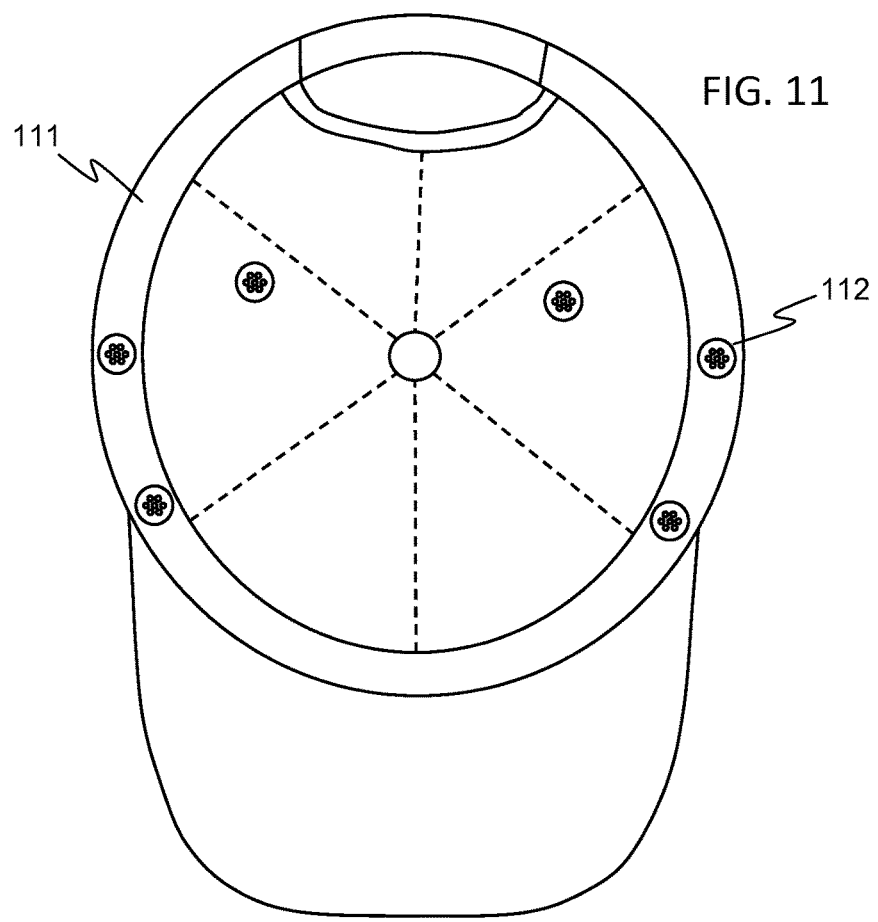
FIG. 11. A ballcap embodiment of the present invention.
Figure 12:
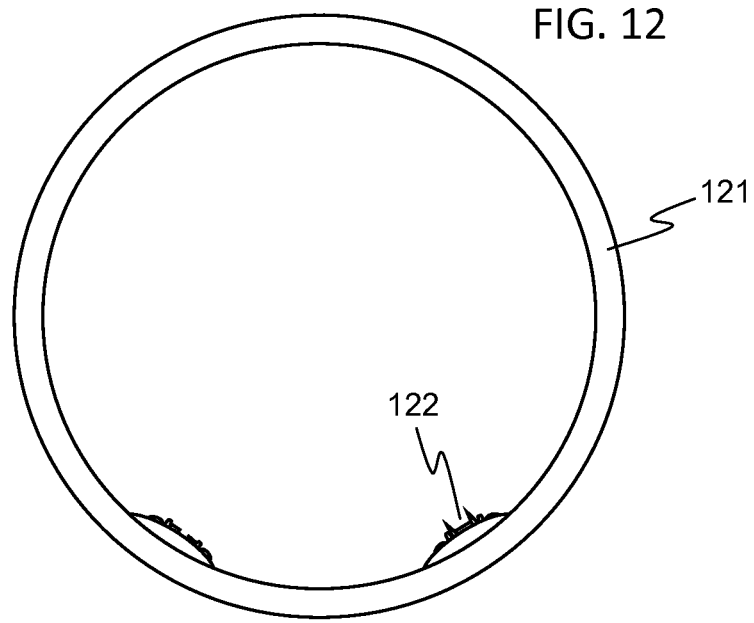
FIG. 12. A headband or sweat band embodiment of the present invention.

FIGS. 10 and 11 show hat and cap embodiments that function similarly to the already-disclosed earbud, eyewear, or helmet embodiments. FIG. 10 shows a head-formed, tight-fitting headwear such as a swim hat or shower cap 101. FIG. 11 shows a baseball cap 111. Dry electrodes 112 and other sensors are integrated into the insides of these hats to permit for measurement of electrophysiological signals, including EOG, ECG, and EEG from the head. Any tight-fitting headpiece, including a running dew rag, can similarly be used to implement the invention. FIG. 12 shows a headband or sweatband 121 with dry electrodes 122 incorporated. As in the other embodiments described, the surface features of the electrodes are advantageous in providing good electrical contact with the skin even when hair is present.

Figure 13:
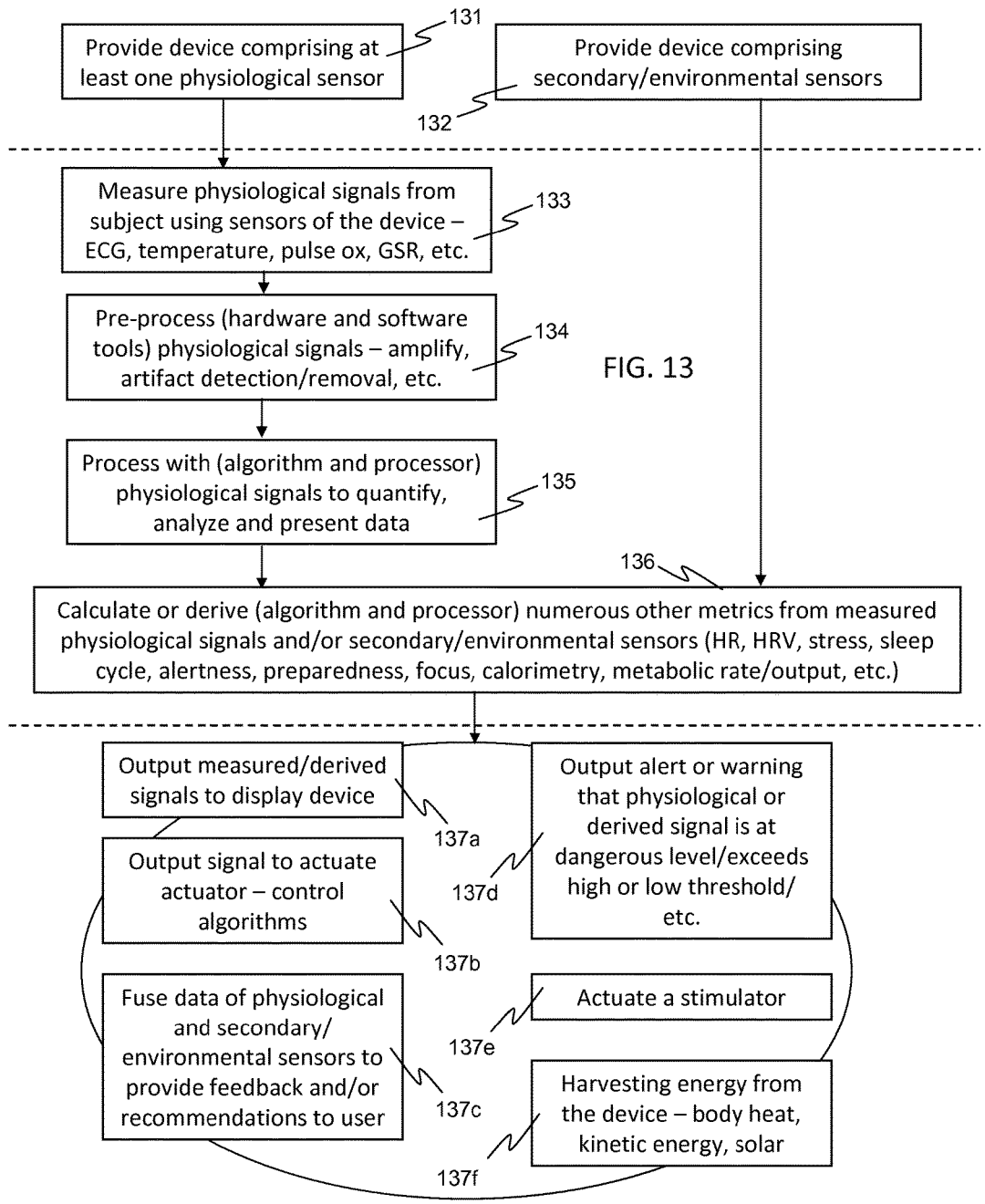
FIG. 13. Flow chart showing various methods of various embodiments of the present invention.
Figure 14:
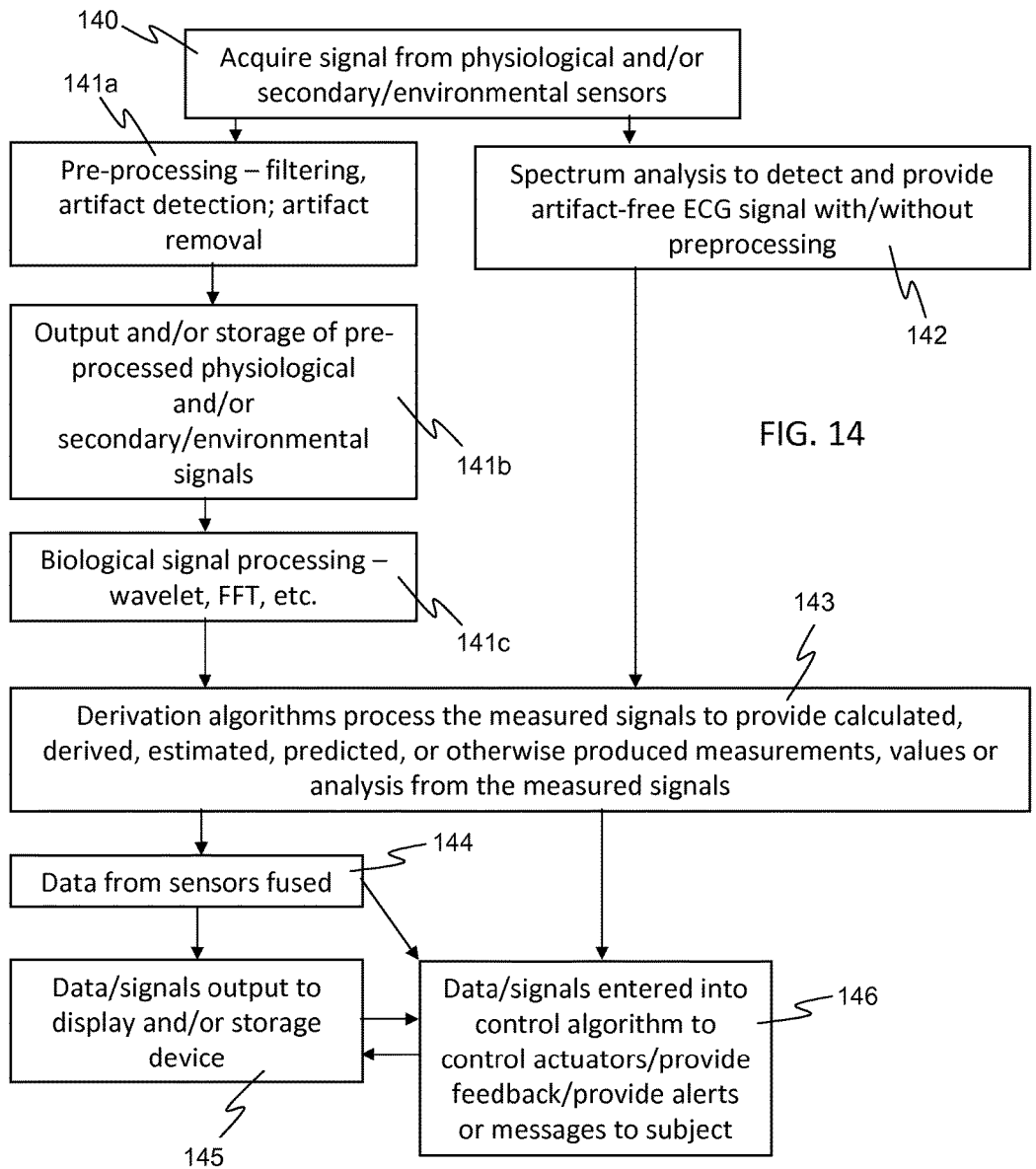
FIG. 14. Flow chart showing various methods of the present invention.

FIGS. 13 and 14 illustrate methods of the present invention in flow chart form. In some embodiments, the method consists of a step 131 of providing a device, such as the earbuds/headphones, eyewear or headgear previously described, comprising at least one physiological sensor of the types previously described. Alternately or in addition, the method consists of a step 132 of providing a device comprising secondary or environmental sensor(s), i.e., sensors that do not directly measure a physiological parameter. The data collected from these sensors can be processed or used in a variety of ways. Typically, physiological data is collected and processed in a series of steps. In one step 133, physiological signal(s) is/are measured from the subject using sensor(s) of the device—including ECG, body temperature, $SpO_2$, GSR, or any of the other listed physiological sensors. In another step 134, the acquired data is pre-processed, either using hardware circuitry or software known in the art to be useful to amplify the signal(s) and detect and remove artifacts from the signal(s). Next 135, the pre-processed signal(s) is/are processed, using an algorithm running on a processor, to quantify, analyze, and present the data. For example, ECG waveforms are analyzed for peaks and interpeak distances.

An optional step 136 of calculating or deriving, using an algorithm running on a processor, numerous other metrics from the measured physiological signal(s) and/or from the secondary/environmental sensor(s). These metrics can include heart rate (as by averaging interpeak distances from an ECG waveform), heart rate variability, stress, sleep cycle, alertness, preparedness, focus, calorimetry, metabolic rate/output, etc. After or before such metrics are calculated, estimated or predicted, any number of steps 137 may be performed. The measured and/or derived signals (if any) may be output to a display device 137a. The signals may be used to actuate one or more of the stimulators 137e or other actuators 137b discussed earlier in this application, such actuators being incorporated into the data acquisition eyewear/headgear/earphones or into a nearby device in communication with the data acquisition device. This actuation may involve various control algorithms that may analyze for feedback the subsequent measured or derived signals, to check for efficacy of the actuation and increase, decrease or alter stimulus as needed. The measured or derived data signals may be fused with data signals from other sensors to provide useful feedback and/or recommendations to the user 137c. An alert or warning can be provided to the subject 137d that a physiological or derived signal is at a dangerous level and/or exceeds a high or low threshold, etc. Finally, the device can harvest energy from the body or the environment 137, e.g., from kinetic or solar energy, using known methods as described above.

In FIG. 14, signals are acquired from physiological and/or secondary/environmental sensors 140. These signals are then (a) pre-processed (with filtering, artifact detection, and artifact removal) 141a; (b) outputted and/or stored 141b; and (c) processed with biological signal processing 141c, using methods including wavelet analysis, FFT analysis, etc. Alternatively or additionally, the originally acquired signals are analyzed with spectrum analysis to detect and provide an artifact-free ECG signal, either with or without preprocessing 142. In either case, derivation algorithms process the measured signals to provide calculated, derived, estimated, predicted, or otherwise produced measurements, values or analysis from the measured signals 143. Data from sensors is fused 144, and data/signals are then output to display and/or storage device 145, or entered into control algorithm to control actuators or provide feedback, alerts, or messages to the subject 146.

As already described in this disclosure, in various embodiments, preferably, the device or system of the present invention derives metrics indicative of one or more of heart rate, heart rate variability, respiration rate, stress, sleep cycle, alertness, concentration, focus, preparedness, calorimetry, or metabolism using one or more of dry electrodes, body temperature sensors, ambient temperature sensors, galvanic skin response sensors, pulse oximetry sensors, near infrared sensors, GPS sensors, accelerometers, gyroscopes, altimeters, pressure sensors, proximity sensors, audio sensors, video sensors, eye tracking sensors, time sensors, data input by the subject, or data sourced from an external database or the Internet, and subsequently supplies a signal, notification, warning, enticement, encouragement, comfort change, plan, or program to the subject using one or more of soundspeakers, video screens, computer interfaces, user interfaces, haptics actuators, shock stimulators, light emitters, temperature actuators, or ear pressure equalizers.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

We claim:

1. A dry electrode method of collecting electrocardiogram (ECG) signals of a subject comprising:

placing on the subject's head a headgear apparatus for acquiring electrophysiological signals, the headgear apparatus comprising a hat, helmet, earpiece or eyeglasses adapted to fit snugly to, and place light pressure on, the head or in an ear of a subject, and a plurality of dry electrodes each comprising a lower surface adapted to contact the subject's skin, the dry electrodes being disposed along and connected to the headgear, the dry electrodes each comprising a plurality of low aspect ratio protruding surface features on the lower surface;

measuring with the dry electrodes of the headgear apparatus at least one electrophysiological signal;

amplifying and filtering the at least one electrophysiological signals to produce ECG signals; and transmitting or storing the ECG signals for collection, wherein the headgear apparatus further comprises at least one other physiological sensor adapted to acquire a non-electrophysiological signal, and further comprising the step of deriving at least one other metric based at least in part on the ECG signals and at least in part on the non-electrophysiological signal, the at least one other metric selected from the group consisting of stress, preparedness, calories expended, oxygen consumption ($VO_2$), maximal oxygen consumption ($VO_2$ max), carbon dioxide production ($VCO_2$), energy expenditure, and respiratory quotient.

2. The method of claim 1, wherein the ECG signals are further processed to determine heart rate.

3. The method of claim 1, wherein the ECG signals are further processed to determine heart rate variability.

4. The method of claim 1, wherein the at least one other derived metric is reported to the subject and forms the basis of a notice or warning delivered to the subject by an automatic output selected from the group consisting of a visual display, an audible alarm, speech, a mild electrical shock, or an ambient or localized temperature change, or a change in the lighting permitted to enter the eyes of the subject.

5. A dry electrode method of providing health information to a subject comprising:

placing on the subject's head a headgear apparatus for acquiring electrophysiological signals, the headgear apparatus comprising a hat, helmet, earpiece or eyeglasses adapted to fit snugly to, and place light pressure on, the head or in an ear of a subject, a plurality of dry electrodes each comprising a lower surface adapted to contact the subject's skin, the dry electrodes being disposed along and connected to the headgear, and at least one other physiological sensor of a different type than electrophysiological, the dry electrodes each comprising a plurality of low aspect ratio protruding surface features on the lower surface;

measuring with the dry electrodes of the headgear apparatus at least one electrophysiological signal; substantially simultaneously, measuring with the at least one other physiological sensor at least one non-electrophysiological signal indicative of a physiological parameter;

deriving at least one physiological metric using at least in part both the at least one electrophysiological signal and the at least one non-electrophysiological signal, wherein the metric is indicative of metabolism, heat loss, calories expended, stress, alertness, or sleep stage; and amplifying and filtering the electrophysiological signals to produce ECG signals.

6. The method of claim 5, further including the steps of placing on the subject's head an eyeglasses apparatus and the step of determining, with a computer processor, when the at least one derived metric has exceeded a threshold or has exhibited a predefined or learned pattern, and automatically providing a stimulus to the subject via a display, alarm, vibrator, buzzer, or stimulus electrode either integrated into the eyeglasses apparatus or integrated into a separate device adapted to be kept on the person of the subject and in communication with the eyeglasses apparatus through either a wired or wireless link.

7. The method of claim 5, wherein the ECG signals are further processed to determine heart rate.

8. The method of claim 5, wherein the ECG signals are further processed to determine heart rate variability.

9. The method of claim 1, wherein the electrode surface features have an aspect ratio of less than 1.5.

10. The method of claim 5, wherein the electrode surface features have an aspect ratio of less than 1.5.

11. The method of claim 1, wherein some of the dry electrodes are adapted to be placed near the eyes and further comprising the step of obtaining EOG signals from the electrodes adapted to be placed near the eyes.

12. The method of claim 5, wherein some of the dry electrodes are adapted to be placed near the eyes and further comprising the step of obtaining EOG signals from the electrodes adapted to be placed near the eyes.

13. A dry electrode method of collecting electrocardiogram (ECG) signals of a subject comprising:

placing on the subject's head a headgear apparatus for acquiring electrophysiological signals, the headgear apparatus comprising a hat, helmet, earpiece or eyeglasses adapted to fit snugly to, and place light pressure on, the head or in an ear of a subject, and a plurality of dry electrodes each comprising a lower surface adapted to contact the subject's skin, the dry electrodes being disposed along and connected to the headgear, the dry electrodes each comprising a plurality of low aspect ratio protruding surface features on the lower surface;

measuring with the dry electrodes of the headgear apparatus at least two electrophysiological signals, at least one electrophysiological signal being an ECG signal; and transmitting or storing the ECG signals for collection, wherein the headgear apparatus further comprises at least one other physiological sensor adapted to acquire a non-electrophysiological signal, and further comprising the step of deriving at least one other metric based at least in part on the ECG signals and at least in part on the non-electrophysiological signal, the at least one other metric selected from the group consisting of stress, preparedness, calories expended, oxygen consumption ($VO_2$), maximal oxygen consumption ($VO_2$ max), carbon dioxide production ($VCO_2$), energy expenditure, and respiratory quotient.

14. The method of claim 13, wherein the ECG signals are further processed to determine heart rate.

15. The method of claim 13, wherein the ECG signals are further processed to determine heart rate variability.

16. The method of claim 13, wherein the electrode surface features have an aspect ratio of less than 1.5.

17. The method of claim 13, wherein some of the dry electrodes are adapted to be placed near the eyes and further comprising the step of obtaining EOG signals from the electrodes adapted to be placed near the eyes.

\* \* \* \* \*